United States Patent
Eros et al.

(10) Patent No.: US 10,688,481 B2
(45) Date of Patent: Jun. 23, 2020

(54) RUTHENIUM COMPLEXES USEFUL FOR CATALYZING METATHESIS REACTIONS

(71) Applicant: XiMo AG, Horw/Lucerne (CH)

(72) Inventors: Gabor Eros, Budapest (HU); Georg Emil Frater, Lucerne (CH)

(73) Assignee: XiMo AG, Zorbig (DE)

( * ) Notice: Subject to any disclaimer, the term of this patent is extended or adjusted under 35 U.S.C. 154(b) by 0 days.

(21) Appl. No.: 16/333,341

(22) PCT Filed: Nov. 9, 2017

(86) PCT No.: PCT/EP2017/078761
§ 371 (c)(1),
(2) Date: Mar. 14, 2019

(87) PCT Pub. No.: WO2018/087230
PCT Pub. Date: May 17, 2018

(65) Prior Publication Data
US 2019/0210012 A1 Jul. 11, 2019

(30) Foreign Application Priority Data

Nov. 9, 2016 (EP) .................... 16002372
Oct. 2, 2017 (EP) .................... 17194384

(51) Int. Cl.
*B01J 31/22* (2006.01)
*C07C 67/475* (2006.01)
*C07F 15/00* (2006.01)

(52) U.S. Cl.
CPC ......... *B01J 31/2273* (2013.01); *B01J 31/226* (2013.01); *B01J 31/2208* (2013.01); *B01J 31/2278* (2013.01); *C07C 67/475* (2013.01); *C07F 15/0046* (2013.01); *B01J 2231/543* (2013.01); *B01J 2531/821* (2013.01); *B01J 2540/20* (2013.01); *B01J 2540/22* (2013.01); *B01J 2540/225* (2013.01); *B01J 2540/442* (2013.01); *B01J 2540/444* (2013.01); *B01J 2540/62* (2013.01); *C07C 2601/16* (2017.05)

(58) Field of Classification Search
CPC .. B01J 31/2273; B01J 31/2208; B01J 31/226; B01J 31/2278; C07C 67/475; C07F 15/0046
(Continued)

(56) References Cited

U.S. PATENT DOCUMENTS

2014/0309433 A1* 10/2014 Marx .................. C07F 15/0046
548/403

FOREIGN PATENT DOCUMENTS

WO  2008046106    4/2008
WO  2014201300   12/2014
WO  WO-2017100585 A1 * 6/2017 ............... C07C 6/06

OTHER PUBLICATIONS

Anderson; Organometallics 2008, 27, 563-566. DOI: 10.1021/om7008028 (Year: 2008).*
(Continued)

*Primary Examiner* — Daniel R Carcanague
(74) *Attorney, Agent, or Firm* — Stoel Rives LLP

(57) ABSTRACT

Compound of formula (4) or formula (5), wherein L is a neutral ligand, preferably a nitrogen-containing heterocyclic carbene (NHC) such as carbene containing at least two nitrogen atoms, a cyclic aminoalkyl carbene (CAAC) or a bicyclic aminoalkyl carbene (BICAAC); $R^1$, $R^3$, $R^4$, $R^5$, $R^6$, $R^7$, $R^8$, $R^9$, $R^{10}$ and $R^{11}$ are, independently, H, unbranched or branched $C_{1-20}$ alkyl, $C_{5-9}$ cycloalkyl, unbranched or branched $C_{1-20}$ alkoxy, optionally bearing one or more halogen atoms, respectively; or aryl, optionally substituted with one or more of unbranched or branched $C_{1-20}$ alkyl, $C_{5-9}$ cycloalkyl, unbranched or branched $C_{1-20}$ alkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl: $R^C$ is H, unbranched or branched $C_{1-20}$ alkyl.

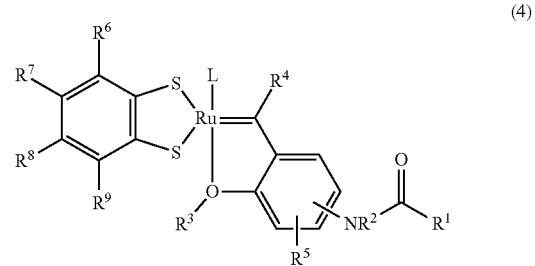

(4)

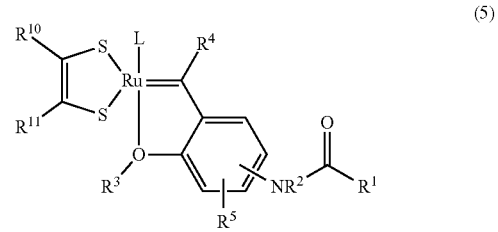

(5)

18 Claims, No Drawings

(58) Field of Classification Search
USPC .............................................................. 549/3
See application file for complete search history.

(56) References Cited

OTHER PUBLICATIONS

Khan; J. Am. Chem. Soc. 2013, 135, 10258-10261. DOI: 10.1021/ja404208a (Year: 2013).*
Rix; J. Org. Chem. 2008, 73, 11, 4225-4228. DOI: 10.1021/jo800203d (Year: 2008).*
International Search Report and Written Opinion dated Feb. 26, 2018 for PCT/EP2017/078761.

* cited by examiner

RUTHENIUM COMPLEXES USEFUL FOR CATALYZING METATHESIS REACTIONS

RELATED APPLICATIONS

This application is a National Stage Entry of International Application No. PCT/EP2017/078761, filed Nov. 9, 2017, which claims priority to European Patent Application No. 17194384.8, filed on Oct. 2, 2017, and to European Patent Application No. 16002372.7, filed on Nov. 9, 2016, each of which is incorporated herein by reference in its entirety.

FIELD OF THE INVENTION

The invention relates to ruthenium complexes bearing a neutral ligand, in particular a nitrogen-containing heterocyclic carbene (NHC)-ligand. The complexes may be used for catalyzing metathesis reactions.

BACKGROUND OF THE INVENTION

Catalytic metathesis has transformed chemical synthesis and offers exceptionally efficient pathways for the synthesis of commercially important chemicals, including but not limited to biologically active molecules, oleochemicals, renewables, fine chemicals, and polymeric materials. Organometallic catalysts based on ruthenium are used in many of such organic transformation reactions.

E.g., U.S. Pat. No. 7,723,255 B1 discloses a transition metal catalyst 1 having the following structure:

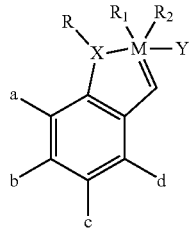

wherein:
M comprises a transition metal such as Ru;
R comprises an alkyl, alkenyl, alkynyl, aryl, alkoxy, alkenyloxy, alkynyloxy, aryloxy, alkoxy carbonyl, alkylamino, alkylthio, alkylsulfonyl, or alkylsulfinyl; each optionally substituted with an alkyl, halogen, aryl or heteroaryl moiety;
$R^1$ and $R^2$ each comprises, or together comprise, an electron withdrawing group;
a, b, c and d each comprise a hydrogen or halogen atom or an alkyl, alkenyl, alkynyl, aryl, alkoxy, alkenyloxy, alkynyloxy, aryloxy, alkoxycarbonyl, alkylamino, alkylthio, alkylsulfonyl or alkylsulfinyl group optionally substituted with an alkyl, halogen, aryl or heteroaryl moiety
X is oxygen, sulfur, nitrogen or phosphorus; and
Y comprises an electron-donating heterocyclic carbene ligand.

Similar structures as in U.S. Pat. No. 7,723,255 B1 are disclosed in EP 1 313 559 B1.

U.S. Pat. No. 6,921,735 discloses ruthenium complexes bearing a 1,3-dimesityl-4,5-dihydroimidazol-2-ylidene and styrenyl ether ligand.

U.S. Pat. No. 6,867,303 B2 discloses a compound of formula 2a,

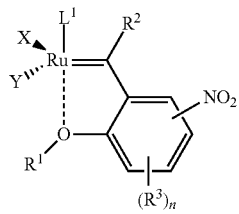

wherein
$L^1$ is a neutral ligand;
X and X' are anionic ligands;
$R^1$ is $C_{1-5}$ alkyl or $C_{5-6}$ cycloalkyl;
$R^2$ is H, $C_{1-20}$ alkyl, $C_{2-20}$ alkenyl, $C_{2-20}$ alkynyl or aryl;
$R^3$ is $C_{1-6}$ alkyl, $C_{1-6}$ alkoxy or aryl, wherein aryl is optionally substituted with $C_{1-6}$ alkyl or $C_{1-6}$ alkoxy;
and n is 0, 1, 2 or 3.

U.S. Pat. No. 8,288,576 discloses a ruthenium catalyst having the following structure 2b:

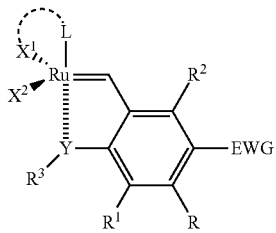

wherein:
$X^1$ and $X^2$ are the same or different and each selected from electron-withdrawing anionic ligands, wherein $X^1$ and $X^2$ may be linked to each other via carbon-carbon and/or carbon-heteroatom bonds;
Y is a neutral two-electron donor selected from oxygen, sulfur, nitrogen or phosphorus;
R is H, halogen atom, alkyl, alkoxy, aryl, aryloxy, alkylcarbonyl, arylcarbonyl, alkoxycarbonyl, aryloxycarbonyl, heteroaryl, carboxyl, cyano, nitro, amido, amino, aminosulfonyl, N-heteroarylsulfonyl, alkylsulfonyl, arylsulfonyl, alkylsulfinyl, arylsulfinyl, alkylthio, arylthio, or sulfonamido group;
$R^1$ and $R^2$ are each H, Br, I, alkyl, alkoxy, aryl, aryloxy, alkylcarbonyl, arylcarbonyl, alkoxycarbonyl, aryloxycarbonyl, carboxyl, amido, amino, heteroaryl, alkylthio, arylthio, or sulfonamido group;
$R^3$ is an alkyl, aryl, heteroaryl, alkylcarbonyl, arylcarbonyl, thiocarbonyl, or aminocarbonyl group;
EWG is chloro or $CO_2Me$; and
L is an electron donating ligand, which may be linked to $X^1$ via carbon-carbon and/or carbon-heteroatom bonds.

Similar compounds as in U.S. Pat. No. 8,049,025 are disclosed in U.S. Pat. No. 7,632,772.

WO 2014/201300 A1 discloses a ruthenium catalyst of formula 3

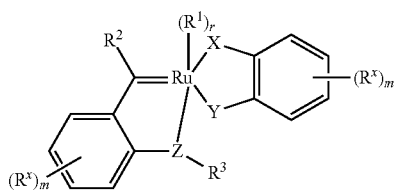

wherein the substituents $R^1$, $R^2$, $R^3$, $R^x$, X, Y, and Z are broadly defined as specified therein.

WO 2017/055945 A1 discloses a ruthenium catalyst represented by the following formula

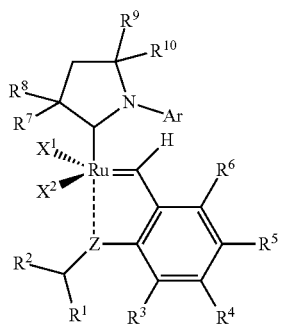

wherein:
$X^1$ and $X^2$ are each independently an anionic ligand selected from halogen atoms, —CN, —SCN, —OR', —SR', —O(C=O)R', —O(SO$_2$)R', and —OSi(R')$_3$ group, wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
Z is an atom selected from a group of O, S, NR', wherein R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
Ar is an aryl group substituted with hydrogen atoms or optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or a halogen atom;
$R^1$ and $R^2$, are each independently hydrogen atom, $C_1$-$C_{25}$ alkyl group, $C_1$-$C_{25}$ alkoxy group, $C_2$-$C_{25}$ alkenyl group, $C_1$-$C_{12}$ perfluoroalkyl, $C_5$-$C_{20}$ aryl, $C_5$-$C_{24}$ aryloxy, $C_5$-$C_{20}$ heteroaryloxy, or can be combined together to form substituted or unsubstituted $C_4$-$C_{10}$ cyclic or $C_4$-$C_{12}$ polycyclic system, can also be an ester (—COOR'), amide (—CONR'$_2$), formyl (—CHO), ketone (—COR'), and hydroxamic (—CON(OR')(R')) group or a halogen atom, in which R' is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom;
$R^3$, $R^4$, $R^5$, $R^6$ are each independently hydrogen atom, sulfoxide group (—S(O)R'), sulphonamide group (—SO$_2$NR'$_2$), phosphonate group (—P(O)(OR')$_2$), phosphinate group (—P(O)R'(OR')), phosphoninum group (—P(OR')$_2$), phosphine group (—PR'$_2$), nitro group (—NO$_2$), nitroso group (—NO), carboxy group (—COOH), ester group (—COOR'), formyl group (—CHO), ketone group (—COR'), wherein R' is $C_1$-$C_5$ alkyl, $C_1$-$C_5$ perfluoroalkyl, $C_5$-$C_{24}$ aryl, $C_7$-$C_{24}$ aralkyl, $C_5$-$C_{24}$ perfluoroaryl;
wherein when $R^1$ and $R^2$ are —CH$_3$ group, then at least one of $R^3$, $R^4$, $R^5$, $R^6$ substituents is not hydrogen atom;
$R^7$, $R^8$, $R^9$, and $R^{10}$ are each independently hydrogen atom or $C_1$-$C_{25}$ alkyl group, $R^7$ and/or $R^8$ can be combined with $R^9$ and/or $R^{10}$ to form cyclic system, are also independently $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, and $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{24}$ aryloxy, $C_5$-$C_{20}$ heteroaryloxy, or a halogen atom.

U.S. Pat. No. 9,249,170 B2 discloses compounds of the following formula

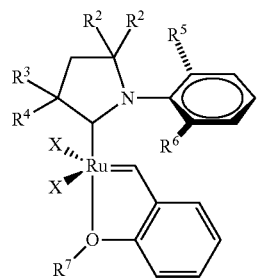

wherein, independently for each occurrence,
X is, independently for each occurrence, alkoxy or halo;
$R^2$ is, independently for each occurrence, alkyl;
$R^3$ is alkyl;
$R^4$ is alkyl, aryl, heteroaryl, aralkyl, or heteroaralkyl;
or $R^3$ and $R^4$, taken together with the carbon atom to which they are attached, form a five-, six-, or ten-membered cycloalkyl or heterocyclyl ring;
$R^5$ is alkyl;
$R^6$ is H or alkyl, provided that (i) $R^5$ and $R^6$ are not the same, and (ii) $R^6$ has fewer atoms than $R^5$; and
$R^7$ is alkyl;
or a compound of formula

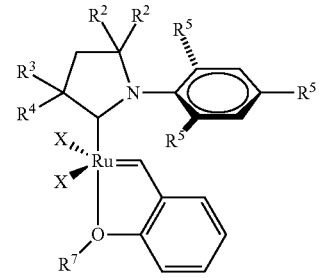

wherein, independently for each occurrence,
X is, independently for each occurrence, alkoxy or halo;
$R^2$ is, independently for each occurrence, alkyl;
$R^3$ is alkyl;
$R^4$ is alkyl, aryl, heteroaryl, aralkyl, or heteroaralkyl;
or $R^3$ and $R^4$, taken together with the carbon atom to which they are attached, form a five-, six-, or ten-membered cycloalkyl or heterocyclyl ring;
$R^5$ is, independently for each occurrence, alkyl; and
$R^7$ is alkyl;

or a compound of formula

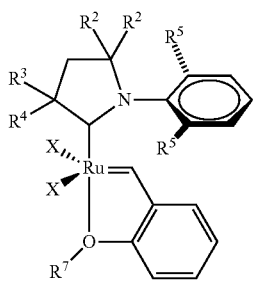

wherein, independently for each occurrence,
X is, independently for each occurrence, alkoxy or halo;
$R^2$ is alkyl;
$R^3$ is alkyl;
$R^5$ is, independently for each occurrence, alkyl;
$R^7$ is alkyl; and
$R^8$ is aryl or heteroaryl;
or a compound of formula

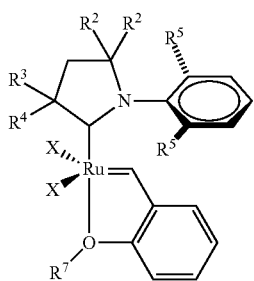

wherein, independently for each occurrence,
X is, independently for each occurrence, alkoxy or halo;
$R^2$ is alkyl;
$R^3$ is alkyl;
$R^5$ is, independently for each occurrence, alkyl;
$R^7$ is alkyl; and
$R^9$ is $C_2$-$C_6$ alkyl;
or $R^3$ and $R^9$, taken together with the carbon atom to which they are attached, form a five-, or ten-membered cycloalkyl or heterocyclyl ring.

OBJECTS OF THE INVENTION

There remains an ongoing need for providing new and improved catalysts useful for catalyzing metathesis reactions, for example, in terms of better catalyst stability and/or activity, efficiency and stereoselectivity.

SUMMARY OF THE INVENTION

The inventors of the present invention discovered that the underlying problem may be solved by selected ruthenium complexes bearing at least an aryliden ligand, a sulfur-based bidentate ligand, and a neutral ligand, the neutral ligand preferably being selected from a nitrogen-containing heterocyclic carbene (NHC).

The invention relates to the following items:
1. A compound of formula 4 or formula 5

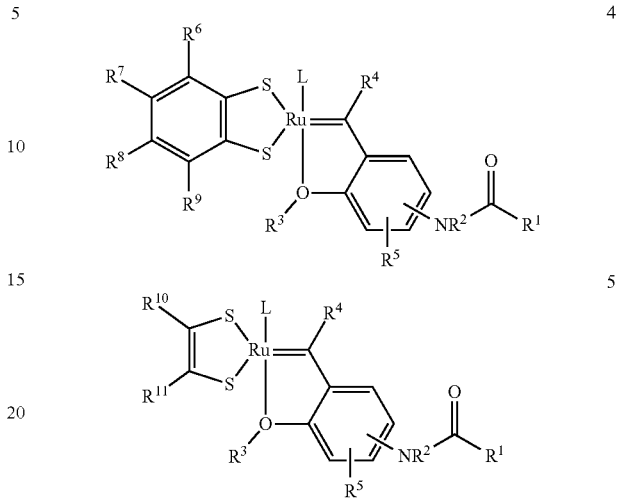

wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:
L is: a neutral ligand;
$R^1$ is: H;
  unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or
  aryl or aryloxy; optionally substituted, respectively, with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;
$R^2$ is: H; unbranched or branched $C_{1-20}$ alkyl; aryl; —C(O)$R^{12}$; —C(O)O$R^{12}$; —C(O)C(O)$R^{12}$; —C(O)C(O)O$R^{12}$; wherein $R^{12}$ has the meaning of $C_{1-20}$ alkyl or aryl, respectively; $R^{12}$ optionally bearing one or more halogen atoms;
$R^3$ is: unbranched or branched $C_{1-20}$ alkyl; aryl; or $R^{13}$—C(O)—CHR$^{14}$—, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is C(O)—O—$C_{1-20}$ alkyl; or wherein $R^{13}$ is $C_{1-20}$ alkyl and $R^{14}$ is H; or $R^{13}$ is OH and $R^{14}$ is H or $C_{1-20}$ alkyl; or $R^{15}$—O—N($R^{16}$)—C(O)—CHR$^{17}$—, wherein $R^{15}$, $R^{16}$, and $R^{17}$ are independently H or $C_{1-20}$ alkyl;
$R^4$ is: H;
$R^5$, $R^6$, $R^7$, $R^8$, $R^9$, $R^{19}$ and $R^{11}$ are, independently, H; unbranched or branched $C_{1-20}$ alkyl; $C_{5-9}$ cycloalkyl or $C_{5-9}$ cycloalkoxy; unbranched or branched $C_{1-20}$ alkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or $N(R^y)(R^z)$, wherein $R^y$ and $R^z$ are independently selected from H and $C_{1-20}$ alkyl; or aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

2. The compound of item 1, wherein in formula 4 or 5 the neutral ligand L is
$P(R^x)_3$, wherein $R^x$ is independently branched or unbranched $C_{1-20}$ alkyl or $C_{1-20}$ alkoxy, $C_{5-9}$ cycloalkyl, or aryl; or
RCN, wherein R is branched or unbranched $C_{1-20}$ alkyl, $C_{5-9}$ cycloalkyl, or aryl; or a nitrogen-containing heterocyclic carbene containing the moiety of formula 6

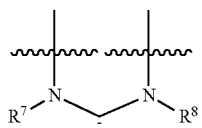

6 wherein $R^7$ and $R^8$ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen, and wherein the chemical bonds which are symbolized with a wiggly line are connected to an optionally substituted alkenylene or alkylene group, respectively, wherein the carbene carbon atom, the two nitrogen atoms and the optionally substituted alkenylene or alkylene group form a ring; or a carbene containing the moiety of formula 7

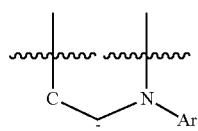

7 wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; and wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group.

3. The compound of item 2, wherein the carbene of formula 6 is a carbene of one of formulas 6a, 6b, 6c or 6d:

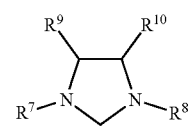

6a

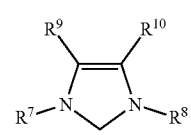

6b

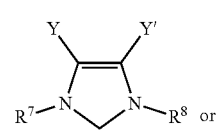

6c

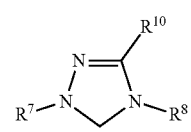

6d wherein $R^9$ and $R^{10}$ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or $R^9$ and $R^{19}$ together with the carbon atoms to which they are attached are combined to form a carbocyclic 3 to 8 membered ring, preferably an aryl ring, more preferably $C_6H_4$;

Y and Y' are halogen.

4. Compound of any one of items 1 to 3, wherein L is of formula 6a or 6b, preferably wherein $R^9$ and $R^{19}$ as defined in formula 6a or 6b are H, respectively, and $R^7$ and $R^9$ as defined in formula 6a and 6b are mesityl, or 2,6-diisopropylphenyl; or wherein L is of formula

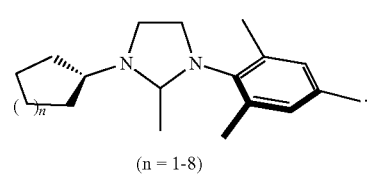

(n = 1-8)

5. The compound of item 2, wherein the carbene of formula 7 is a carbene of one of formulas 7a or 7b:

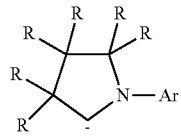

7a wherein each R in formula 7a is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_5$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein two R which are separated by the C—$CR_2$—C moiety can be combined with to form a cyclic system;

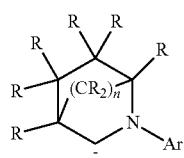

7b wherein each R in formula 7b is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein n is 1, 2 or 3; preferably wherein R in formula 7b are each independently hydrogen, $C_1$-$C_{12}$ alkyl, or $C_3$-$C_{12}$ cycloalkyl.

6. The compound of item 5, wherein the ligand of formula 7a is of formula 7a'

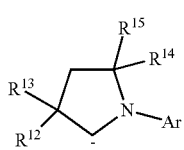

7a' wherein $R^{12}$, $R^{13}$, $R^{14}$, and $R^{15}$ in formula 7a' are each independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein $R^{12}$ and/or $R^{13}$ can be combined with $R^{14}$ and/or $R^{15}$ to form a cyclic system; or wherein the ligand of formula 7b is of formula 7b':

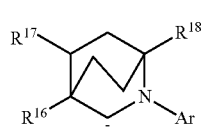

7b' wherein $R^{16}$, $R^{17}$ and $R^{18}$ in formula 7b' are each independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom, preferably wherein $R^{16}$, $R^{17}$ and $R^{18}$ in formula 7b' are each independently hydrogen, $C_1$-$C_{12}$ alkyl, or $C_3$-$C_{12}$ cycloalkyl.

7. The compound of any one of items 2, 5 or 6, wherein L in formula 4 or 5 is a carbene of formula 7c

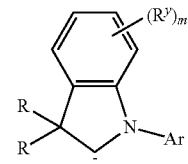

7c wherein m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; such as a carbene of formula 7c'

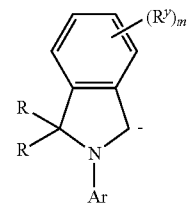

7c' or is a carbene of formula 7d

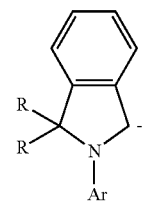

7d wherein m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; such as a carbene of formula 7d'

7d' or is a carbene of formula 7e

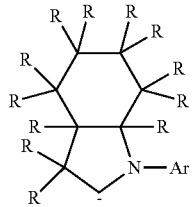

or is a carbene of formula 7f

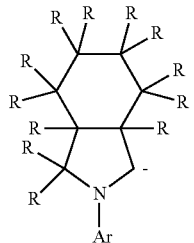

or is carbene of formula 7g or 7h

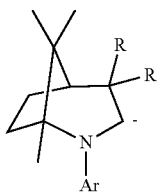

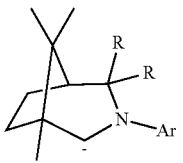

or is a carbene of formula 7i

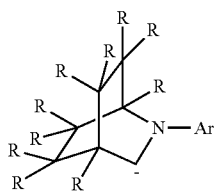

or is a carbene of formula 7k

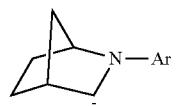

wherein each R in one of formulas 7c to 7i is independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{24}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or a halogen atom; preferably wherein each R in formulae 7c to 7i is hydrogen, $C_1$-$C_{12}$ alkyl, or $C_3$-$C_{12}$ cycloalkyl.

8. Compound of any one of the preceding items, wherein $R^1$ in formula 4 or 5 is $C_{1-6}$ alkyl, optionally substituted with one or more of halogen, or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or N($R^y$)($R^z$), wherein $R^y$ and $R^z$ are independently selected from H and $C_{1-20}$ alkyl.

9. Compound of any one of the preceding items, wherein $R^2$ in formula 4 or 5 is H.

10. Compound of any one of the preceding items, wherein $NR^2$—C(O)—$R^1$ in formula 4 or 5 is in para-position with respect to O.

11. Compound of any one of the preceding items, wherein $R^3$ in formula 4 or 5 is methyl or isopropyl.

12. Compound of any one of the proceeding items, wherein $R^5$ in formula 4 or 5 is H.

13. Compound of any one of the preceding items, wherein $R^6$, $R^7$, $R^8$, and $R^9$ in formula 4 are independently selected from H and halogen.

14. Compound of any one of items 1 to 13, wherein $R^{10}$ and $R^{11}$ as defined in formula 5 are independently selected from halogen and cyano.

15. Compound, wherein the compound has the structure of formula I-c:

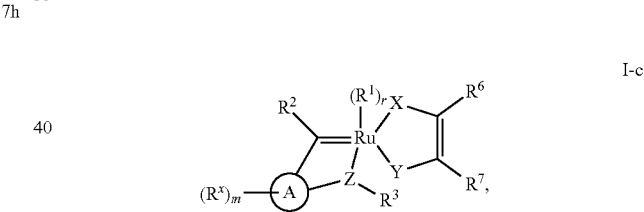

I-c wherein:
each of $R^6$ and $R^7$ is independently R, —CN, halogen, —OR, —OC(O)R, —OSiR_3, —SR, —S(O)R, —S(O)_2R, —NO_2, —N(R')_2, —NR'C(O)R, —NR'C(O)OR, —NR'C(O)N(R')_2, —NR'SO_2R, —NR'SO_2N(R')_2, —NR'OR, —SeR, —SiR_3; or
$R^6$ and $R^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur; or
wherein the compound has the structure of formula I-d:

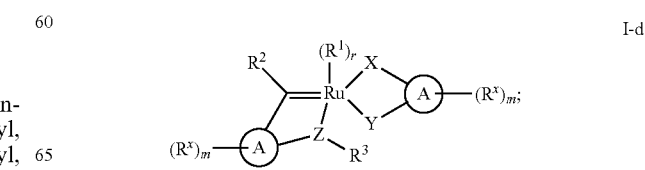

I-d or wherein the compound has the structure of formula I-e:

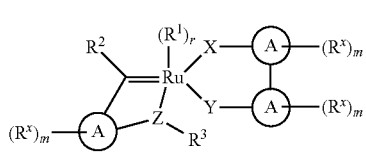

I-e or wherein the compound has the structure of formula I-f:

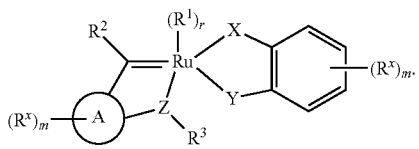

I-f wherein
R¹ is a nitrogen-containing carbene containing the moiety of formula 7

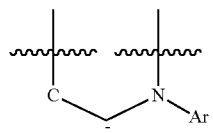

7 wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_6$-$C_{14}$ aryloxy, or halogen; and
wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group;
r is 1 or 2, preferably 1;
X and Y are —S—;
Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;
each $R^x$ is independently halogen, R, —CN, —C(O)N(R')₂, —C(O)R, —C(O)OR, —OR, —OC(O)R, —OC(O)OR, —OC(O)N(R)₂, —OSiR₃, —N(R')₂, —N(R)₃⁺, —NR'C(O)R, —NR'C(O)OR, —NR'C(O)N(R')₂, —NR'SO₂R, —NR'SO₂N(R')₂, —NR'OR, —NO₂, —SiR₃, —PR₂, —P(O)R₂, —P(O)(OR)₂, —SR, —SC(O)R, —S(O)R, —SO₂R, —SO₃R, —SO₂N(R')₂, or —SeR;
each R' is independently R, —C(O)R, —C(O)NR₂, —C(O)OR, —SO₂R, —SO₂NR₂, —P(O)(OR)₂, or —OR; and
each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;
m is 0-6;
R² is $R^x$;
R³ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; and
Z is —O— or —S—.

16. Compound of item 15, wherein the compound has the structure of formula I-g:

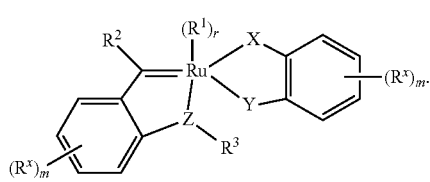

I-g

17. Compound of item 15 or 16, wherein the carbene is of formula 7a or 7b:

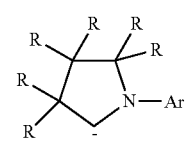

7a wherein each R in formula 7a is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein two R which are separated by the C—CR₂—C moiety can be combined with to form a cyclic system; or

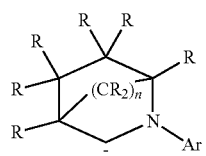

7b wherein each R in formula 7b is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein n is 1, 2 or 3; preferably wherein R in formula 7b are each independently hydrogen, $C_1$-$C_{12}$ alkyl, or $C_3$-$C_{12}$ cycloalkyl.

18. The compound of item 17, wherein the carbene of formula 7a is of formula 7a'

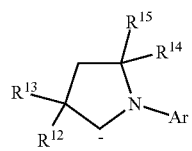

7a' wherein $R^{12}$, $R^{13}$, $R^{14}$, and $R^{15}$ in formula 7a are each independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein $R^{12}$ and/or $R^{13}$ can be combined with $R^{14}$ and/or $R^{15}$ to form a cyclic system; or wherein the carbene of formula 7b is of formula 7b':

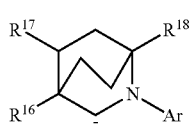

7b' wherein $R^{16}$, $R^{17}$ and $R^{18}$ in formula 7b' are each independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom, preferably wherein $R^{16}$, $R^{17}$ and $R^{18}$ in formula 7b' are each independently hydrogen, $C_1$-$C_{12}$ alkyl, or $C_3$-$C_{12}$ cycloalkyl.

19. The compound of any one of items 15 to 18, wherein L in formula 4 or 5 is a carbene of formula 7c

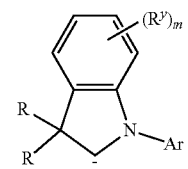

7c wherein in formula 7c m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; such as a carbene of formula 7c'

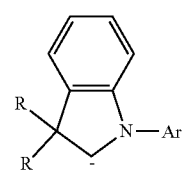

7c' or is a carbene of formula 7d

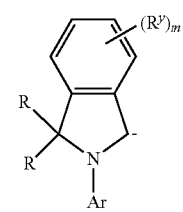

7d wherein in formula 7d m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; such as a carbene of formula 7d'

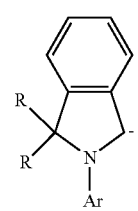

7d' or is a carbene of formula 7e

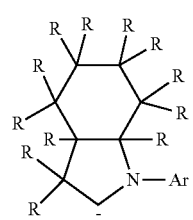

7e or is a carbene of formula 7f

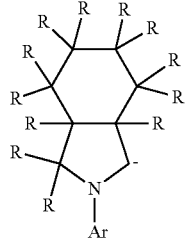

7f or is a carbene of formula 7g or 7h

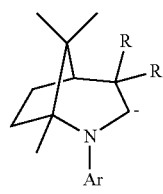

7g

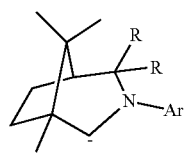

7h or is a carbene of formula 7i

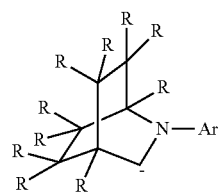

7i or is a carbene of formula 7k

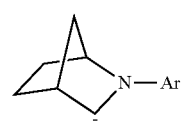

7k wherein each R in formulas 7c to 7i is independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; preferably each R in formulae 7c to 7i is hydrogen, $C_1$-$C_{12}$ alkyl, or $C_3$-$C_{12}$ cycloalkyl.

20. Compound of any one of items 15 to 19, wherein Z is —O—.

21. Compound of any one of the preceding items, wherein the compound is selected from one of compounds E1 to E12:

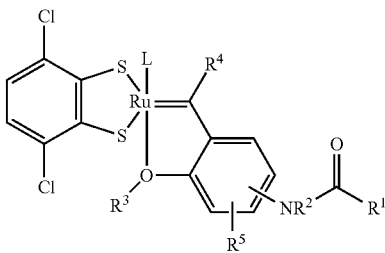

E1

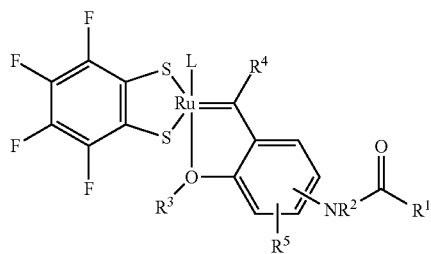

E2

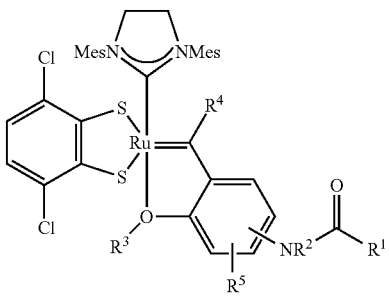

E3

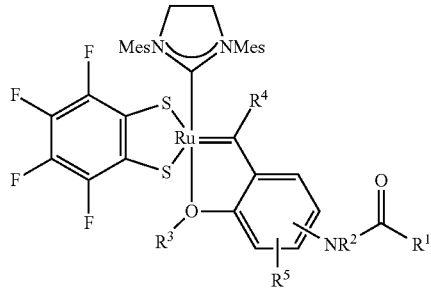

E4

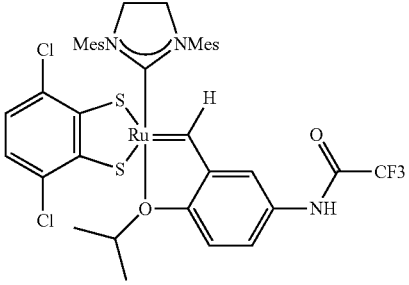

E5

-continued

E6 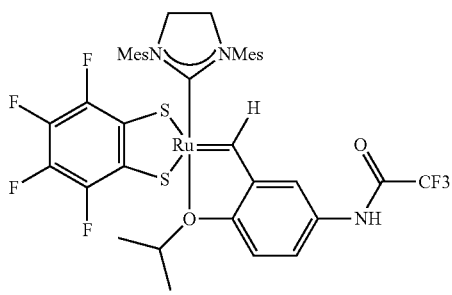

E7 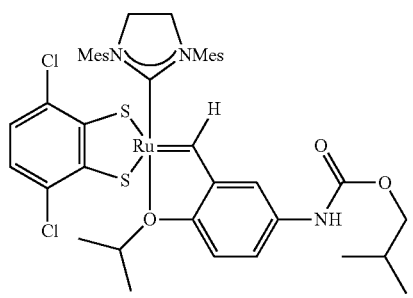

E8 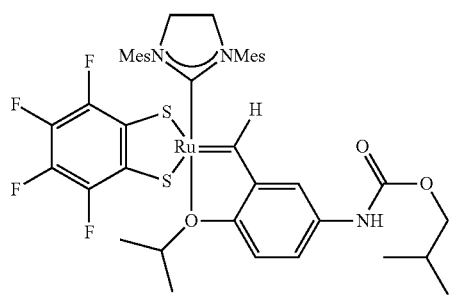

E9 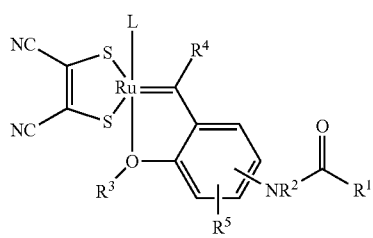

E10 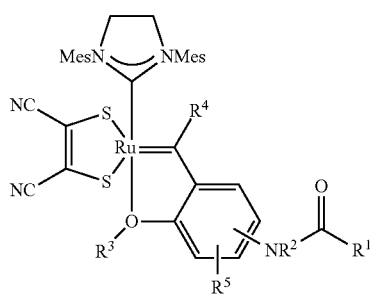

-continued

E11 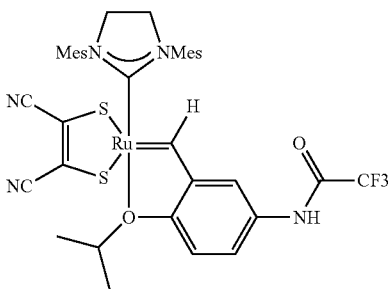

E12 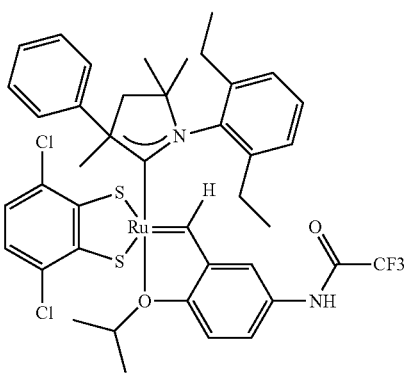

22. Compound of any one of items 15 to 21, wherein the compound is not a compound of formula 4 or formula 5

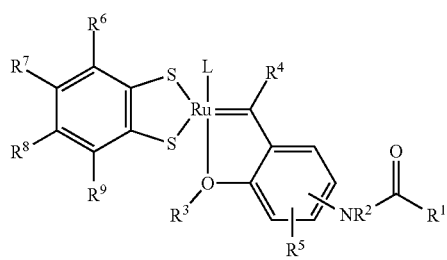
4

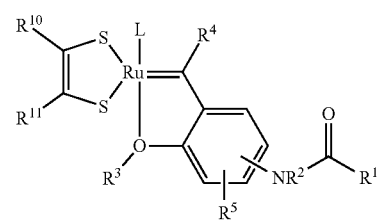
5 wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is: a neutral ligand;

$R^1$ is: H;
  unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or
  aryl or aryloxy; optionally substituted, respectively, with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H; unbranched or branched $C_{1-20}$ alkyl; aryl; —C(O)$R^{12}$; —C(O)O$R^{12}$; —C(O)C(O)$R^{12}$; —C(O)C(O)O$R^{12}$; wherein $R^{12}$ has the meaning of $C_{1-20}$ alkyl or aryl, respectively; $R^{12}$ optionally bearing one or more halogen atoms;

$R^3$ is: unbranched or branched $C_{1-20}$ alkyl; aryl; or $R^{13}$—C(O)—CH$R^{14}$, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is C(O)—O—$C_{1-20}$ alkyl; or wherein $R^{13}$ is $C_{1-20}$ alkyl and $R^{14}$ is H; or $R^{13}$ is OH and $R^{14}$ is H or $C_{1-20}$ alkyl; or $R^{15}$—O—N($R^{16}$)—C(O)—CH$R^{17}$, wherein $R^{15}$, $R^{16}$, and $R^{17}$ are independently H or $C_{1-20}$ alkyl;

$R^4$ is: H;

$R^5$, $R^6$, $R^7$, $R^8$, $R^9$, $R^{10}$ and $R^{11}$ are, independently, H; unbranched or branched $C_{1-20}$ alkyl or unbranched or branched $C_{1-20}$ alkoxy; $C_{5-9}$ cycloalkyl or $C_{5-9}$ cycloalkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or $N(R^y)(R^z)$, wherein $R^y$ and $R^z$ are independently selected from H and $C_{1-20}$ alkyl; or aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl; and wherein in formula 4 or 5 the neutral ligand L is a carbene containing the moiety of formula 7

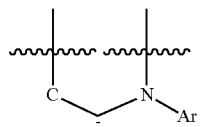

7 wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_6$-$C_{14}$ aryloxy, or halogen; and wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group.

23. Compound of any one of the preceding items, wherein the compound is immobilized on a solid support.

24. Method of catalysing a metathesis reaction, comprising providing a compound as defined in any one of claims 1 to 23.

25. Method of item 24, further comprising providing one or more olefins, wherein more than 80% of the olefins formed in the catalysed metathesis reaction are Z-olefins.

DETAILED DESCRIPTION OF THE INVENTION

All terms in quotation marks are defined in the meaning of the invention.

In a first aspect, the invention relates to a compound of formula 4 or formula 5:

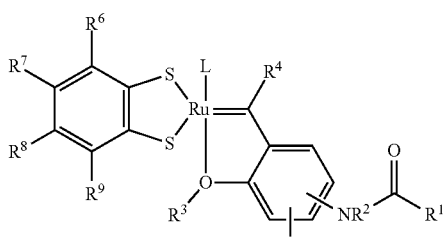

4

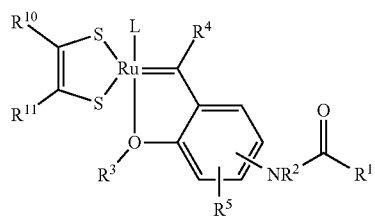

5 wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is: a neutral ligand;

$R^1$ is: H;

unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or aryl or aryloxy; optionally substituted, respectively, with one or more of unbranched or branched $C_{1-20}$ alkyl, $C_{5-9}$ cycloalkyl, unbranched or branched $C_{1-20}$ alkoxy, $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H; unbranched or branched $C_{1-20}$ alkyl; aryl; —C(O)$R^{12}$; —C(O)O$R^{12}$; —C(O)C(O)$R^{12}$; —C(O)C(O)O$R^{12}$; wherein $R^{12}$ has the meaning of $C_{1-20}$ alkyl or aryl, respectively; $R^{12}$ optionally bearing one or more halogen atoms;

$R^3$ is: unbranched or branched $C_{1-20}$ alkyl; aryl; or $R^{13}$—C(O)—CH$R^{14}$, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is C(O)—O—$C_{1-20}$ alkyl; or wherein $R^{13}$ is $C_{1-20}$ alkyl and $R^{14}$ is H; or $R^{13}$ is OH and $R^{14}$ is H or $C_{1-20}$ alkyl; or $R^{15}$—O—N($R^{16}$)—C(O)—CH$R^{17}$, wherein $R^{15}$, $R^{16}$, and $R^{17}$ are independently H or $C_{1-20}$ alkyl;

$R^4$ is: H;

$R^5$, $R^6$, $R^7$, $R^8$, $R^9$, $R^{10}$ and $R^{11}$ are, independently, H; unbranched or branched $C_{1-20}$ alkyl or unbranched or branched $C_{1-20}$ alkoxy; $C_{5-9}$ cycloalkyl or $C_{5-9}$ cycloalkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or N($R^y$)($R^z$), wherein $R^y$ and $R^z$ are independently selected from H and $C_{1-20}$ alkyl; or aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or N($R^y$)($R^z$), wherein $R^y$ and $R^z$ are independently selected from H and $C_{1-20}$ alkyl.

In a preferred embodiment, the term "$C_{1-20}$ unbranched or branched alkyl" means $C_{1-6}$ alkyl.

The term "unbranched or branched $C_{1-20}$ alkyl, unbranched or branched $C_{1-20}$ alkoxy, $C_{5-9}$ cycloalkyl, $C_{5-9}$ cycloalkoxy, optionally bearing one or more halogen atoms" encompasses in a preferred embodiment perhalogenated residues.

Preferred perhalogenated residues are $CCl_3$, $CF_3$, $C_2F_5$, $C_3F_7$, $C_4F_9$, $C_5F_{11}$, $C_6F_{13}$, $C_7F_{15}$ and $C_5F_{17}$.

In particular with respect to $R^1$, the term "$C_{1-20}$ unbranched or branched alkyl (optionally) bearing one or more halogen atoms" encompasses in a preferred embodiment perhalogenated residues. Preferred perhalogenated residues are $CCl_3$, $CF_3$, $C_2F_5$, $C_3F_7$, $C_4F_9$, $C_5F_{11}$, $C_6F_{13}$, $C_7F_{15}$ and $C_5F_{17}$.

The term "aryl" encompasses $C_6$, $C_{10}$ and $C_{14}$ aryl. A preferred aryl residue is phenyl or naphthyl.

In one embodiment, each aryl residue may be optionally substituted with one or more of unbranched or branched $C_{1-20}$ alkyl, $C_{5-9}$ cycloalkyl, unbranched or branched $C_{1-20}$ alkoxy, $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen, or N($R^y$)($R^z$), wherein $R^y$ and $R^z$ are independently selected from H and $C_{1-20}$ alkyl.

In one embodiment, the neutral ligand L is a phosphine.

Preferably, the neutral ligand is of formula P($R^x$)$_3$, wherein $R^x$ is independently branched or unbranched $C_{1-20}$ alkyl or $C_{1-20}$ alkoxy, $C_{5-9}$ cycloalkyl, or aryl. In a preferred embodiment, $R^x$ is cyclohexyl.

In one embodiment, the neutral ligand is a nitrile.

Preferably, the nitrile is of formula RCN, wherein R is branched or unbranched $C_{1-20}$ alkyl, $C_{5-9}$ cycloalkyl, or aryl.

In a preferred embodiment, the neutral ligand L in formula 4 or 5 is a nitrogen-containing carbene, preferably an electron-donating nitrogen-containing carbene.

In one embodiment, the carbene is a N-heterocyclic carbene (NHC).

In one embodiment, the N-heterocyclic carbene (NHC) contains at least two nitrogen atoms.

Preferably, the carbene contains the moiety of formula 6

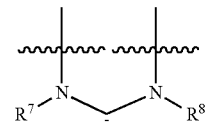

6 wherein $R^7$ and $R^8$ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen; and wherein the chemical bonds which are symbolized with a wiggly line are connected to an optionally substituted alkenylene or alkylene group, respectively, wherein the carbene carbon atom, the two nitrogen atoms and the optionally substituted alkenylene or alkylene group form a ring.

Suitable optional substituents of the optionally substituted alkenylene or alkylene groups are e.g. $C_{1-10}$ alkyl, $C_{3-10}$ cycloalkyl, $C_{1-10}$ alkoxyl, $C_{3-10}$ cycloalkoxyl phenyl, or halogen.

The electrons at the carbene carbon atom form a bond with Ru.

In a preferred embodiment, neutral ligand L is a carbene derived from formula 6 or comprising formula 6.

In one embodiment, the neutral ligand L in formula 4 or 5 is a carbene of one of formulas 6a, 6b, 6c or 6d:

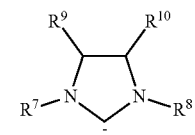

6a

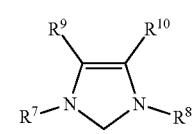

6b

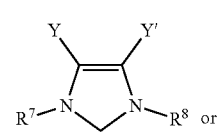

6c or

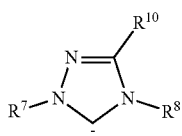

In formulas 6a to 6d, $R^7$ and $R^8$ as defined therein are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen;

$R^9$ and $R^{10}$ as defined therein are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or $R^9$ and $R^{10}$ together with the carbon atoms to which they are attached are combined to form an carbocyclic 3 to 8 membered ring, preferably an aryl ring, more preferably $C_6H_4$; and Y and Y' are halogen.

In one embodiment, the carbene is an unsaturated carbene of formula 6a or 6b, preferably 6a.

In one embodiment, the carbene is unsymmetrically substituted, wherein preferably in formula 6a or 6b $R^9=R^{10}=H$ and $R^7$ and $R^9$ are different.

In one embodiment, L is an unsymmetrical nitrogen-heterocyclic carbene, preferably

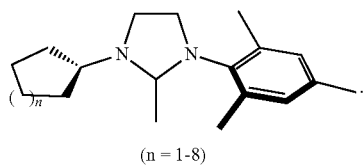

(n = 1-8)

In another embodiment, the electron-donating nitrogen-containing heterocyclic carbene contains only one nitrogen atom.

In one embodiment, the electron-donating carbene is a cyclic (CAAC) or bicyclic (BICAAC) aminoalkyl carbene 7:

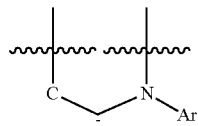

wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; and wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group.

Suitable optional substituents of the optionally substituted alkenylene or alkylene groups are e.g. $C_{1-10}$ alkyl, $C_{3-10}$ cycloalkyl, $C_{1-10}$ alkoxyl, $C_{3-10}$ cycloalkoxyl phenyl, or halogen.

In one embodiment, the CAAC ligand is of formula 7a

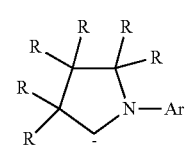

wherein each R in formula 7a is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein two R which are separated by the C—$CR_2$—C moiety can be combined with to form a cyclic system In one embodiment, the CAAC ligand is of formula 7a'

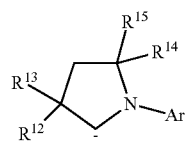

wherein $R^{12}$, $R^{13}$, $R^{14}$, and $R^{15}$ in formula 7a are each independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein $R^{12}$ and/or $R^{13}$ can be combined with $R^{14}$ and/or $R^{15}$ to form a cyclic system.

In another embodiment, the BICAAC ligand is of formula 7b:

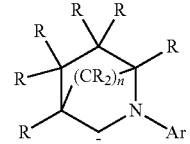

wherein each R in formula 7b is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein n is 1, 2 or 3; preferably wherein $R^{16}$, $R^{17}$ and $R^{18}$ in formula 7b are each independently hydrogen, $C_1$-$C_{12}$ alkyl, or $C_3$-$C_{12}$ cycloalkyl.

In one embodiment, the BICAAC ligand is of formula 7b'

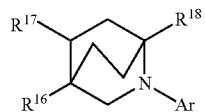
7b' wherein $R^{16}$, $R^{17}$ and $R^{18}$ in formula 7b' are each independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom, preferably wherein $R^{16}$, $R^{17}$ and $R^{18}$ in formula 7b' are each independently hydrogen, $C_1$-$C_{12}$ alkyl, or $C_3$-$C_{12}$ cycloalkyl.

In further embodiments, the CAAC or BICAAC ligand is of one of the following structures 7c to 7k, i.e. a carbene of structure 7c

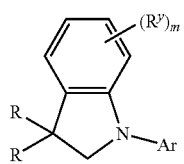
7c wherein in formula 7c m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; such as a carbene of formula 7c'

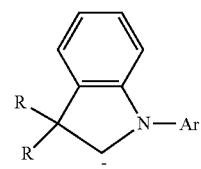
7c' or is a carbene of formula 7d

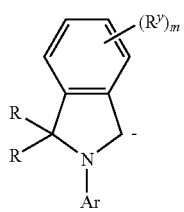
7d wherein in formula 7d m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen;

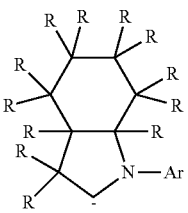
7d' or is a carbene of formula 7e

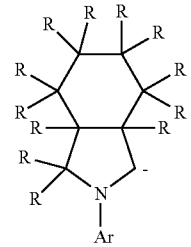
7e or is a carbene of formula 7f

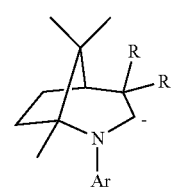
7f or is a carbene of formula 7g or 7h

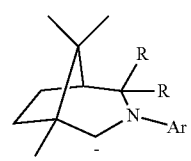
7g

7h or is a carbene of formula 7i

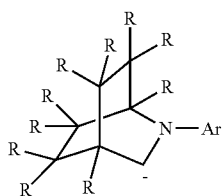

or is a carbene of formula 7k

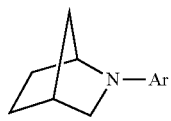

wherein each R in formulas 7c to 7i is independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_5$-$C_{14}$ aryloxy, or a halogen atom; preferably each R in formulae 7c to 7i is hydrogen, $C_1$-$C_{12}$ alkyl, or $C_3$-$C_{12}$ cycloalkyl.

In one embodiment, in a compound of formula 4 or 5, $R^1$ is $C_{1-6}$ alkyl, optionally substituted with one or more of halogen; or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl.

In one embodiment, $R^2$ is H.

In another embodiment, —$NR^2$—C(O)—$R^3$ is in para-position with respect to O.

In one embodiment, $R^3$ is methyl or isopropyl.

In one embodiment, $R^4$ is H.

In one embodiment, $R^5$ is H.

In one embodiment, $R^6$, $R^7$, $R^8$, and $R^9$ as defined in formula 4 are independently selected from H and halogen. Preferably, halogen is Cl, Br or F.

In one embodiment, $R^{10}$ and $R^{11}$ as defined in formula 5 are independently selected from halogen and cyano.

In a preferred embodiment, $R^{10}$ and $R^{11}$ as defined in formula 5 are cyano.

In one embodiment, L is of formula 6a or 6b.

In a preferred embodiment, $R^9$ and $R^{10}$ as defined in formula 6a or 6b are H, respectively, and $R^7$ and $R^8$ as defined in formula 6a and 6b are mesityl, respectively; or 2,6-diisopropylphenyl, or 2,4,6-triisopropylphenyl, respectively.

In another embodiment, $R^9$ and $R^{10}$ as defined in formula 6a or 6b are H, respectively, and $R^7$ and $R^8$ as defined in formula 6a and 6b are 2,6-diisopropylphenyl 2,4,6-triiso- propylphenyl, respectively, or 2,6-dihalogenophenyl, respectively, or 2,4,6-trihalogenophenyl.

In one embodiment, in a compound of formula 4 or 5, $R^1$ is $C_{1-6}$ alkyl, optionally substituted with one or more of halogen, or phenyl, optionally substituted with one or more of unbranched or branched $C_{1-20}$ alkyl, $C_{5-9}$ cycloalkyl, unbranched or branched $C_{1-20}$ alkoxy, $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;
$R^2$ is H;
$R^3$ is methyl or isopropyl;
$R^4$ is H;
$R^5$ is H;
$R^6$, $R^7$, $R^8$, and $R^9$ in formula 4 are independently selected from H and halogen;
$R^{10}$ and $R^{11}$ in formula 5 are independently selected from halogen and cyano;
L is of formula 6a or 6b.

In one embodiment, $R^1$ is $C_{1-6}$ alkyl, optionally substituted with one or more of halogen, or phenyl, optionally substituted with one or more of unbranched or branched $C_{1-20}$ alkyl, $C_{5-9}$ cycloalkyl, unbranched or branched $C_{1-20}$ alkoxy, $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;
$R^2$ is H;
$NR^2$—C(O)—$R^3$ is in para-position with respect to O;
$R^3$ is methyl or isopropyl;
$R^4$ is H;
$R^5$ is H;
$R^6$, $R^7$, $R^8$, and $R^9$ in formula 4 are independently selected from H and halogen;
$R^{10}$ and $R^{11}$ in formula 5 are independently selected from halogen and cyano;
L is of formula 6a or 6b, wherein $R^9$ and $R^{10}$ as defined in formula 6a or 6b are H, respectively, and $R^7$ and $R^8$ as defined in formula 6a and 6b are mesityl, 2,6-diisopropyl, or 2,4,6-triisopropyl, respectively.

In one embodiment, the invention relates to compounds E1 to E12 falling under the general formulas 4 or 5

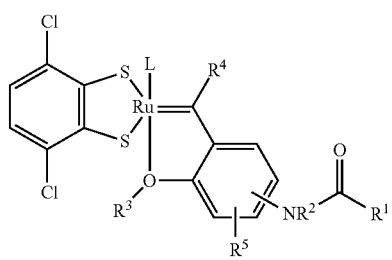

E1

E2
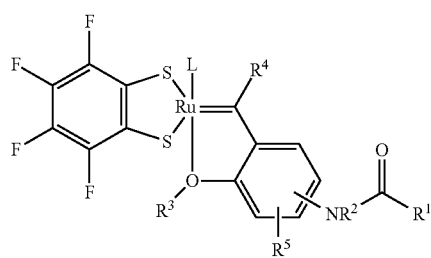
E3
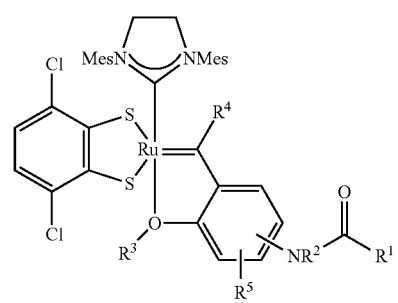
E4
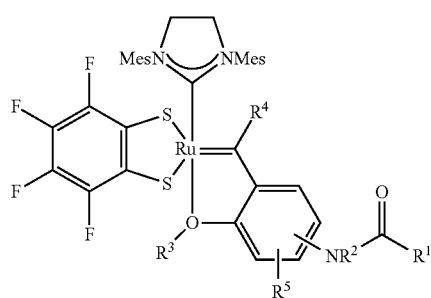
E5
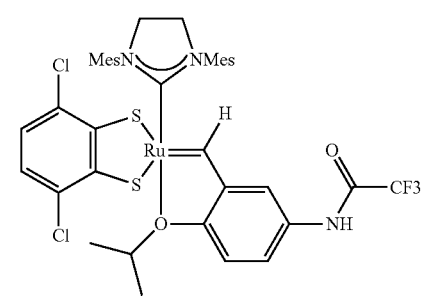
E6
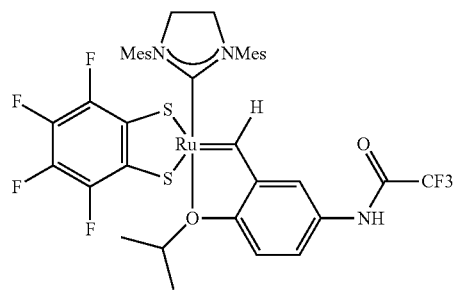
E7
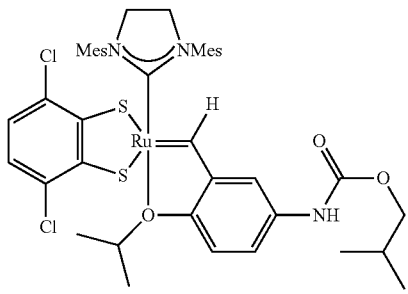
E8
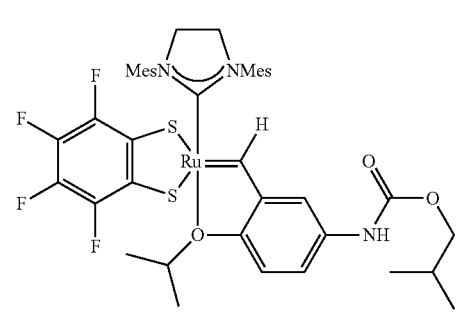
E9
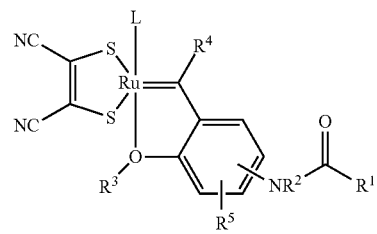
E10
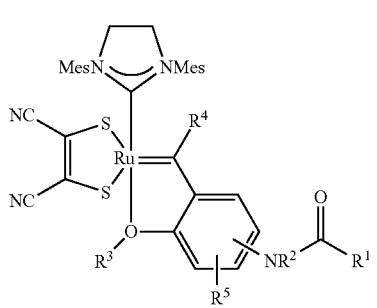
E11
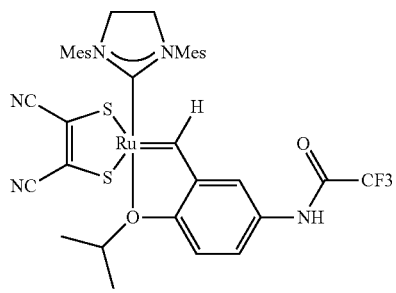

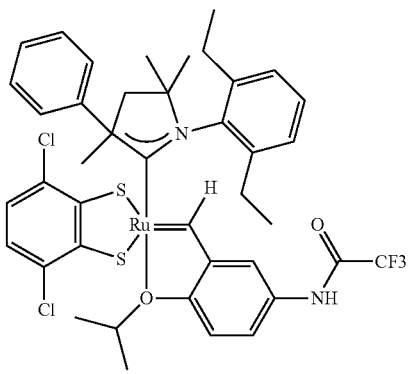

E12

Preferably, L in E1 and E2 is a NHC ligand.

The amide function —NR$^2$—C(O)—R$^1$ in formula 4 and formula 5 can act as a spacer for the introduction of an ion marker ("tag") for immobilization in an aqueous and/or ion phase as well as on a solid support. Such an ion marking enables better recycling of the catalytic complexes to be performed in aqueous/ion solvents or on a solid support (continuous flow reaction) and thus enables a clear reduction in the cost of the reaction while avoiding contamination of high added value products, in particular in the context of a pharmaceutical molecule synthesis process.

Accordingly, in one embodiment, the compound of formula 4 or 5 is immobilized in an aqueous and/or ion phase or on a solid support.

The invention further relates to a compound of formula 4 or formula 5:

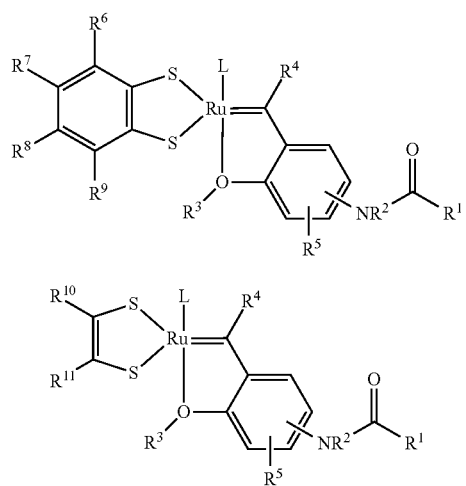

wherein the substituents L and R$^1$, R$^2$, R$^3$, R$^4$, R$^5$, R$^6$, R$^7$, R$^8$, R$^9$, R$^{10}$ and R$^{11}$ have the following meaning:

L is a neutral ligand;

R$^1$, R$^3$, R$^4$, R$^5$, R$^6$, R$^7$, R$^8$, R$^9$, R$^{10}$ and R$^{11}$ are, independently, H, unbranched or branched C$_{1-20}$ alkyl, C$_{5-9}$ cycloalkyl, unbranched or branched C$_{1-20}$ alkoxy, C$_{5-9}$ cycloalkoxy; optionally bearing one or more halogen atoms, respectively; or aryl, optionally substituted with one or more of unbranched or branched C$_{1-20}$ alkyl, C$_{5-9}$ cycloalkyl, unbranched or branched C$_{1-20}$ alkoxy, aryl, aryloxy, unbranched or branched C$_{1-20}$ alkylcarbonyl, arylcarbonyl, unbranched or branched C$_{1-20}$ alkoxycarbonyl, aryloxycarbonyl, heteroaryl, carboxyl, cyano, nitro, amido, aminosulfonyl, N-heteroarylsulfonyl, unbranched or branched C$_{1-20}$ alkylsulfonyl, arylsulfonyl, unbranched or branched C$_{1-20}$ alkylsulfinyl, arylsulfinyl, unbranched or branched C$_{1-20}$ alkylthio, arylthio, sulfonamide, halogen, or N(R$^y$)(R$^z$), wherein R$^y$ and R$^z$ are independently selected from H and C$_{1-20}$ alkyl;

R$^2$ is H, or unbranched or branched C$_{1-20}$ alkyl.

In one embodiment,

R$^1$ is H, unbranched or branched C$_{1-20}$ alkyl, C$_{5-9}$ cycloalkyl, unbranched or branched C$_{1-20}$ alkoxy or C$_{5-9}$ cycloalkoxy; optionally bearing one or more halogen atoms, respectively; or aryl or aryloxy, optionally substituted with one or more of unbranched or branched C$_{1-20}$ alkyl, C$_{5-9}$ cycloalkyl, unbranched or branched C$_{1-20}$ alkoxy, C$_{5-9}$ cycloalkoxy, aryl, aryloxy, unbranched or branched C$_{1-20}$ alkylcarbonyl, arylcarbonyl, unbranched or branched C$_{1-20}$ alkoxycarbonyl, aryloxycarbonyl, heteroaryl, carboxyl, cyano, nitro, amido, N(R$^y$)(R$^z$), wherein R$^y$ and R$^z$ are independently selected from H and C$_{1-20}$ alkyl, aminosulfonyl, N-heteroarylsulfonyl, unbranched or branched C$_{1-20}$ alkylsulfonyl, arylsulfonyl, unbranched or branched C$_{1-20}$ alkylsulfinyl, arylsulfinyl, unbranched or branched C$_{1-20}$ alkylthio, arylthio, sulfonamide, or halogen;

R$^2$ is H, unbranched or branched C$_{1-20}$ alkyl;

R$^3$ is H, unbranched or branched C$_{1-20}$ alkyl, or aryl;

R$^4$ is H, unbranched or branched C$_{1-20}$ alkyl, or aryl;

R$^5$, R$^6$, R$^7$, R$^8$, R$^9$, R$^{10}$ and R$^{11}$ are, independently, H, unbranched or branched C$_{1-20}$ alkyl, C$_{5-9}$ cycloalkyl, unbranched or branched C$_{1-20}$ alkoxy or C$_{5-9}$ cycloalkoxy, optionally bearing one or more halogen atoms, respectively; or Aryl or aryloxy, optionally substituted with one or more of unbranched or branched C$_{1-20}$ alkyl, C$_{5-9}$ cycloalkyl, unbranched or branched C$_{1-20}$ alkoxy, C$_{5-9}$ cycloalkoxy, aryl, aryloxy, unbranched or branched C$_{1-20}$ alkylcarbonyl, arylcarbonyl, unbranched or branched C$_{1-20}$ alkoxycarbonyl, aryloxycarbonyl, heteroaryl, carboxyl, cyano, nitro, amido, aminosulfonyl, N-heteroarylsulfonyl, unbranched or branched C$_{1-20}$ alkylsulfonyl, arylsulfonyl, unbranched or branched C$_{1-20}$ alkylsulfinyl, arylsulfinyl, unbranched or branched C$_{1-20}$ alkylthio, arylthio, sulfonamide, halogen or N(R$^y$)(R$^z$), wherein R$^y$ and R$^z$ are independently selected from H and C$_{1-20}$ alkyl.

In an alternative aspect, the invention relates to a compound of formula 4 or formula 5

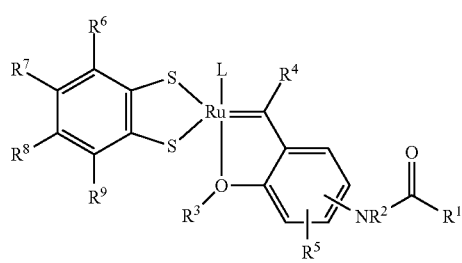

4

-continued

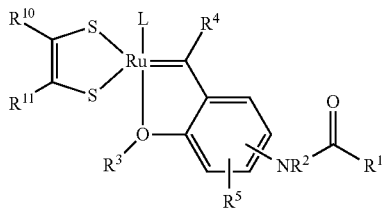

wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is a neutral ligand;

$R^1$, $R^2$, $R^5$, $R^6$, $R^7$, $R^8$, $R^9$, $R^{10}$ and $R^{11}$ are, independently, a hydrogen, a $C_1$ to $C_6$ alkyl, a $C_1$ to $C_6$ perhalogenoalkyl, a residue of an aldehyde, a residue of a ketone, a residue of an ester, a residue of an amide, a nitrile, a cyano, an optionally substituted aryl, a pyridinium alkyl, a pyridinium perhalogenoalkyl or an optionally substituted $C_5$ or $C_6$ cyclohexyl, a $C_nH_{2n}Y$ or $C_nF_{2n}Y$ radical with n being between 1 and 6 and Y being an ion marker;

$R^2$ can also be hydrogen or a $C_1$ to $C_6$ alkyl;

$R^3$ is a $C_1$ to $C_6$ alkyl or a $C_5$ or $C_6$ cycloalkyl or a $C_5$ or $C_6$ aryl;

$R^4$ is independently, hydrogen, a $C_1$ to $C_6$ alkyl, a $C_1$ to $C_6$ perhalogenoalkyl, or a $C_5$ or $C_6$ aryl.

In a further aspect, the invention relates to a compound of formula I-c:

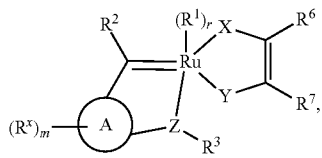

wherein:

each of $R^6$ and $R^7$ is independently R, —CN, halogen, —OR, —C(O)R, —OSiI$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —SiI$_3$, or $R^6$ and $R^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur; or wherein the compound has the structure of formula I-d:

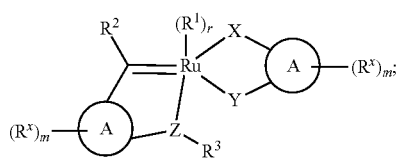

or wherein the compound has the structure of formula I-e:

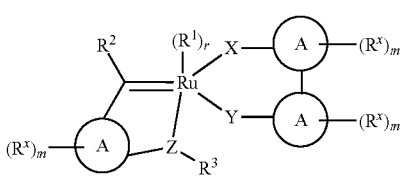

or wherein the compound has the structure of formula I-f:

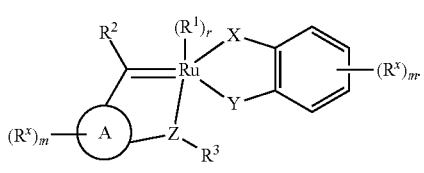

wherein $R^1$ is a nitrogen-containing heterocyclic carbene (NHC) containing at least two nitrogen atoms or a cyclic aminoalkyl carbene (CAAC) or a bicyclic aminoalkyl carbene (BI-CAAC) as defined with respect to L in the first aspect above;

r is 1 or 2, preferably 1;

X and Y are —S—;

Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

each $R^x$ is independently halogen, R, —CN, —C(O)N(R')$_2$, —C(O)R, —C(O)OR, —OR, —OC(O)R, —C(O)OR, —C(O)N(R')$_2$, —OSiI$_3$, —N(R')$_2$, —N(R')$_3^+$, —NR'C(O)R, —NR'C(O)OR, —NR'C(O)N(R')$_2$, —NR'SO$_2$R, —NR'SO$_2$N(R')$_2$, —NR'OR, —NO$_2$, —SiI$_3$, —PI$_2$, —P(O)I$_2$, —P(O)(OR)$_2$, —SR, —SC(O)R, —S(O)R, —SO$_2$R, —SO$_3$R, —SO$_2$N(R')$_2$, or —SeR;

each R' is independently R, —C(O)R, —C(O)NI$_2$, —C(O)OR, —SO$_2$R, —SO$_2$NI$_2$, —P(O)(OR)$_2$, or —OR; and each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

m is 0-6;

$R^2$ is $R^x$;

$R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; and Z is —O— or —S—.

In one embodiment, the compound has the structure of formula I-g:

I-g

In one embodiment, the compound is not a compound of formula 4 or formula 5 as defined in the first aspect,

4

5 wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is: a neutral ligand;

$R^1$ is: H;
unbranched or branched $C_{1-20}$ alkyl or unbranched or branched $C_{1-20}$ alkoxy; $C_{5-9}$ cycloalkyl or $C_{5-9}$ cycloalkoxy; optionally bearing one or more halogen atoms, respectively; or
aryl or aryloxy; optionally substituted, respectively, with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H; unbranched or branched $C_{1-20}$ alkyl; aryl; —C(O)$R^{12}$; —C(O)O$R^{12}$; —C(O)C(O)$R^{12}$; —C(O)C(O)O$R^{12}$; wherein $R^{12}$ has the meaning of $C_{1-20}$ alkyl or aryl, respectively; $R^{12}$ optionally bearing one or more halogen atoms;

$R^3$ is: unbranched or branched $C_{1-20}$ alkyl; aryl; or $R^{13}$—C(O)—CHR$^{14}$, wherein $R^{13}$ is $C_{1-20}$ alkoxy and $R^{14}$ is H or $C_{1-20}$ alkyl; or wherein $R^{13}$ is $C_{1-20}$ alkoxy and $R^{14}$ is C(O)—O—$C_{1-20}$ alkyl; or wherein $R^{13}$ is $C_{1-20}$ alkyl and $R^{14}$ is H; or $R^{13}$ is OH and $R^{14}$ is H or $C_{1-20}$ alkyl; or $R^{15}$—O—N($R^{16}$)—C(O)—CHR$^{17}$, wherein $R^{15}$, $R^{16}$, and $R^{17}$ are independently H or $C_{1-20}$ alkyl;

$R^4$ is: H;

$R^5$, $R^6$, $R^7$, $R^8$, $R^9$, $R^{10}$ and $R^{11}$ are, independently, H; unbranched or branched $C_{1-20}$ alkyl or unbranched or branched $C_{1-20}$ alkoxy; $C_{5-9}$ cycloalkyl or $C_{5-9}$ cycloalkoxy; aryl; aryloxy; unbranched or branched $C_{1-20}$ alkylcarbonyl; arylcarbonyl; unbranched or branched $C_{1-20}$ alkoxycarbonyl; aryloxycarbonyl; heteroaryl; carboxyl; cyano; nitro; amido; aminosulfonyl; N-heteroarylsulfonyl; unbranched or branched $C_{1-20}$ alkylsulfonyl; arylsulfonyl; unbranched or branched $C_{1-20}$ alkylsulfinyl; arylsulfinyl; unbranched or branched $C_{1-20}$ alkylthio; arylthio; sulfonamide; halogen; or $N(R^y)(R^z)$, wherein $R^y$ and $R^z$ are independently selected from H and $C_{1-20}$ alkyl; or
aryl or aryloxy, respectively substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl; and wherein in formula 4 or 5 the neutral ligand L is a nitrogen-containing carbene containing the moiety of formula 7

7 wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen; and wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group.

Compounds according to the invention may be prepared according to methods which are described in the Example section below. Some of said methods are known in the art.

E.g., in one embodiment, a suitable thiocatechol zinc salt or a suitable ethane 1,2-dithiol zinc salt is reacted with a suitable dichloro ruthenium precursor complex to afford a compound of general formula 4 or 5.

Thiocatechole and ethane 1,2-dithiols are known in the art or may be prepared according to known methods.

Dichloro ruthenium complexes are also known in the art or may be prepared according to known methods.

NHC carbenes of formula 6, e.g. 6a to 6d, are known in the art and may be prepared according to known methods (see e.g. prior art as referred to in the Background section)

CAAC carbenes of formula 7 such as 7a are known in the art and may be prepared according to known methods (see e.g. WO 2017/055945 A1; Eur. J. Inorg. Chem. 2017, 3362-3375; ACS Catal. 2017, 5443-5449; Angew. Chem. Int. Ed. 2015, 54, 1919-1923).

BICAAC carbenes of formula 7b are known in the art and may be prepared according to known methods (see e.g. J. Am. Chem. Soc. 2017, 139, 7753-7756).

The new ruthenium complexes may be used for catalysing a metathesis reaction. Preferably, the metathesis reaction is a metathesis reaction of one or more olefins.

Accordingly, in a second aspect, the invention relates to a method of catalysing a metathesis reaction, comprising providing a compound as defined in the first aspect.

In one embodiment, the method further comprises providing one or more olefins, wherein more than 80% of the olefins formed in the catalysed metathesis reaction are Z-olefins.

In a preferred embodiment, more than 85% or more than 90% or more than 95% of the olefins formed in the catalysed metathesis reaction are Z-olefins.

EXAMPLES

Preparation of Thiocatecholate Zinc Salts

Suitable thiocatecholate zinc salts in the form of complexes may be prepared by reacting an aryl 1,2-dithiol with ethylenediamine in the presence of a zinc salt such as zinc acetate:

3,6-Dichlorobenzene-1,2-dithiolate Zinc 10

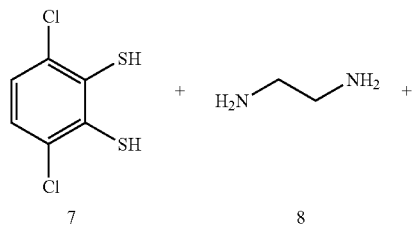

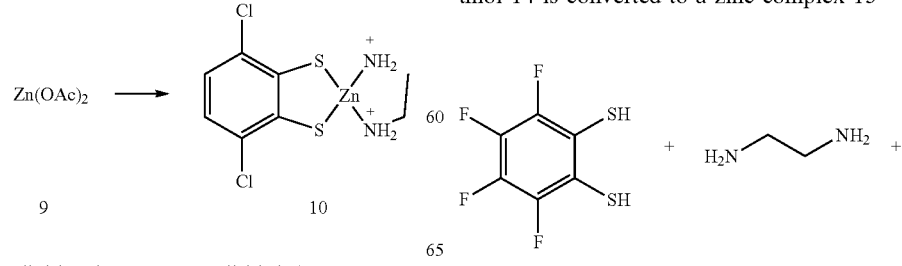

A mixture of 3,6-dichlorobenzene-1,2-dithiol (7, 211 mg, 1.00 mmol, 1.00 equiv) purchased from Aldrich, $Zn(Oac)_2 \cdot 2H_2O$ (9, 878 mg, 4.00 mmol, 4.00 equiv) and ethylenediamine (8, 0.40 mL, 6.00 mmol, 6.00 equiv) in i-PrOH (8 mL) was allowed to stir for one hour at 22° C. The precipitated solid was filtered, washed with methanol (5.0 mL) and hot chloroform (5.0 mL), and dried in a vacuum desiccator overnight to afford 10 (261 mg, 0.95 mmol, 95% yield) as white solid.

Suitable aryl 1,2-thiolates may be prepared by reacting a suitable arene with sulfur in the presence of a strong base such as an alkyl lithium:

3,4,5,6-Tetrafluorobenzene-1,2-dithiolate Zinc 15

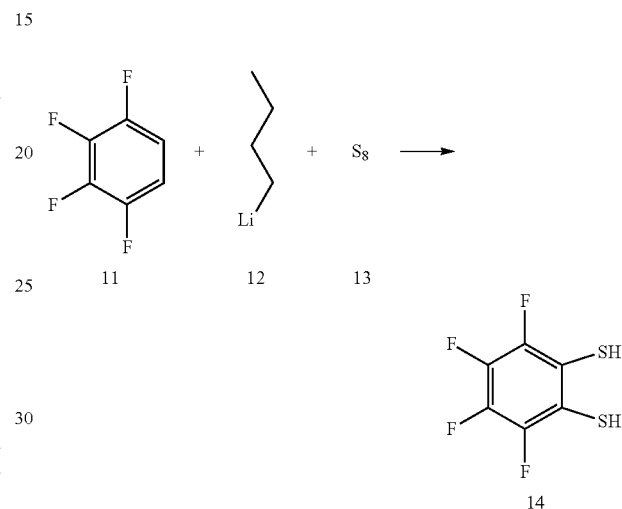

To a stirred solution of n-BuLi (12, 0.69 mL, 1.10 mmol, 1.10 equiv) in tetrahydrofuran (2 mL) at −78° C. was added 1,2,3,4-tetrafluorobenzene (11, 150 mg, 1.00 mmol, 1.00 equiv) over 30 minutes, after which the solution was allowed to stir for 45 minutes at −78° C. Then, powdered anhydrous sulfur (13, 35.3 mg, 1.10 mmol, 1.10 equiv) was added in portions over 30 minutes followed by vigorous stirring for 30 minutes at −78° C. Then a solution of n-BuLi (12, 0.69 mL, 1.10 mmol, 1.10 equiv) in hexane (0.5 mL) at −78° C. was added followed by powdered anhydrous sulfur (13, 35.3 mg, 1.10 mmol, 1.10 equiv) in portions over 30 minutes then stirring for 30 minutes at −78° C. The reaction was quenched with cold 6M HCl (1.5 mL) and extracted with $Et_2O$ (3×5.0 mL). The combined organic layers were washed with water (10 mL), dried over anhydrous $MgSO_4$, and filtered and concentrated in vacuo to give (150.0 mg, 0.82 mmol, 82% yield) 3,4,5,6-tetrafluorobenzene-1,2-dithiol 14 as yellow oil.

In a subsequent step, 3,4,5,6-tetrafluorobenzene-1,2-dithiol 14 is converted to a zinc complex 15

-continued

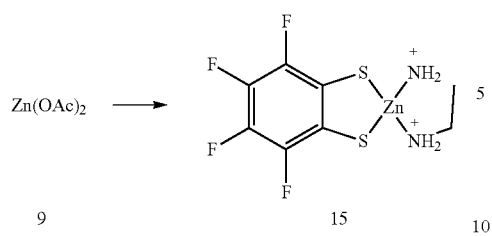

9   15

A mixture of dithiol 14 (471 mg, 2.20 mmol, 1.00 equiv), Zn(Oac)$_2$·2H$_2$O (9, 1932 mg, 8.80 mmol, 4.00 equiv) and ethylenediamine (8, 0.88 mL, 13.20 mmol, 6.00 equiv) in i-PrOH (16 mL) was allowed to stir for three hours at 22° C. The precipitated solid was filtered, washed with methanol (5.0 mL) and hot chloroform (5.0 mL), and dried in a vacuum desiccator overnight to afford 3,4,5,6-tetrafluorobenzene-1,2-dithiolate Zinc 15 (470 mg, 1.39 mmol, 63% yield) as white solid.

Preparation of Ru Complexes According to the Invention Using Suitable Ru Precursor Complexes The Ru precursors are known from the prior art as e.g. referred to in the Background section or may be produced according to known methods.

General procedure for the synthesis of dithiolate Ru complexes:

The reaction according to the general procedure is schematically shown in the following scheme using a Ru dichloro complex bearing a NHC ligand containing two nitrogen atoms which is reacted with a suitable dithiolate complex to afford a compound E6 according to the invention:

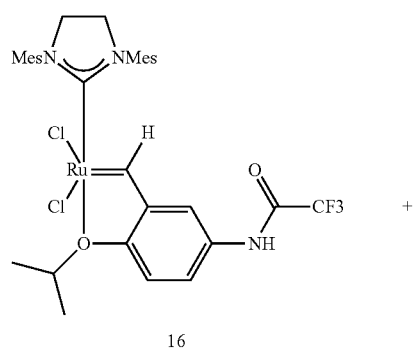

16

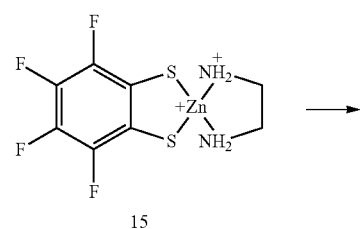

15

-continued

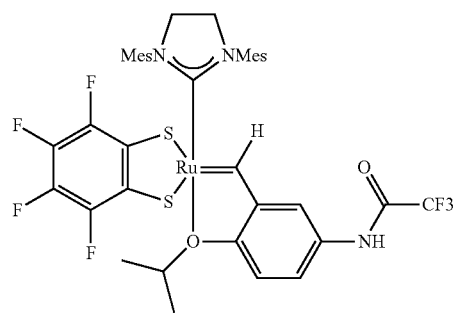

E6

To a 4 mL vial charged with stir bar and zinc dithiolate 10 or 15 (0.098 mmol, 2.00 equiv) under N$_2$ atmosphere, a solution of dichloro ruthenium complex (0.049 mmol, 1.00 equiv) in tetrahydrofuran (650 μL) was added and allowed to stir at 22° C. Reaction progress was monitored by $^1$H NMR spectroscopy. Upon >97% conversion after two to five hours, the solvent was evaporated under vacuum. Residual tetrahydrofuran was removed through co-evaporation with dichloromethane (2×2 mL). The obtained solid was dissolved in dichloromethane and filtered. After removal of dichloromethane from the filtrate, complexes were isolated as green solids.

Ruthenium complex E6 was synthetized according to the general procedure and isolated in the form of a green solid (35 mg, 0.04 mmol, 57% yield). $^1$H-NMR (C6D6): δ=1.46 (d, 3H, C$\underline{H}_3$CHCH$_3$), 1.69 (br, 6H, CH$_3$ Mes), 1.75 (d, 3H, CH$_3$CHC$\underline{H}_3$), 2.17 (s, 6H, CH$_3$ Mes), 2.54 (s, 6H, CH$_3$ Mes), 3.98 (br, 4H, CH$_2$ NHC), 5.41 (sept, 1H, CH$_3$C$\underline{H}$CH$_3$), 6.25 (br, 1H, CH Mes), 6.60 (br, 1H, CH Mes), 6.96 (br, 2H, CH Mes), 6.80 (d, J=2.3 Hz, 1H, C6-H), 7.27 (d, J=9.0 Hz, 1H, C3-H), 7.78 (dd, J=2.3 Hz, 9.0 Hz, 1H, C4-H), 10.11 (s, 1H, NH), 14.30 ppm (s, 1H, Ru═CH).

$^{19}$F-NMR (C$_6$D$_6$): δ=−76.4 (s), −139.8 (ddd), −144.8 (ddd), −166.4 (ddd), −167.3 ppm (ddd).

$^{13}$C-NMR (C$_6$D$_6$): δ=19.9 (CH$_3$ Mes), 21.5 (C$\underline{H}_3$ CHCH$_3$), 23.8 (CH$_3$CHC$\underline{H}_3$), 52.8 (CH$_2$ NHC), 84.0 (CH$_3$ $\underline{C}$HCH$_3$), 116.8 (C6), 117.0 (C3), 118.6 (C4), 129.8 (CH Mes), 130.0 (CH Mes), 132.7 (C5), 135.5 (C Mes), 137.1 (C Mes), 139.1 (C Mes), 142.6 (C1), 152.5 (C2), 251.4 ppm (Ru═CH).

Ruthenium complex E5 was synthetized according to the general procedure

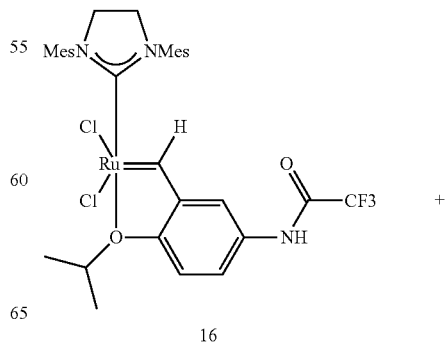

16

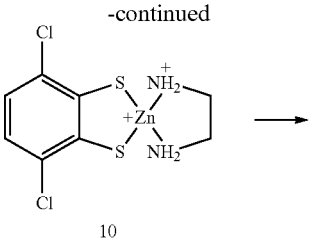

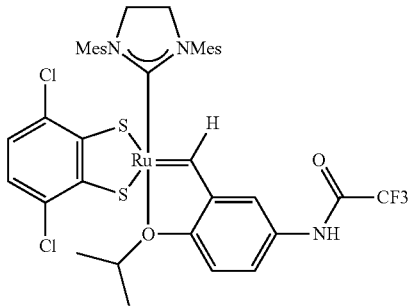

E5 and isolated in the form of a green solid (36 mg, 0.04 mmol, 59% yield). $^1$H-NMR (C$_6$D$_6$): δ=1.47 (d, 3H, C$\underline{H}_3$CHCH$_3$), 1.64 (br, 6H, CH$_3$ Mes), 1.72 (d, 3H, CH$_3$CHC$\underline{H}_3$), 2.17 (s, 6H, CH$_3$ Mes), 2.55 (br, 6H, CH$_3$ Mes), 3.97 (br, 4H, CH$_2$ NHC), 5.40 (sept, 1H, CH$_3$C$\underline{H}$CH$_3$), 6.30 (br, 1H, CH Mes), 6.50 (br, 1H, CH Mes), 6.94 (br, 2H, CH Mes), 6.72&6.82 (Abq, 2H, C3'-H, C4'-H), 6.77 (d, J=2.3 Hz, 1H, C6-H), 7.24 (d, J=9.0 Hz, 1H, C3-H), 7.77 (dd, J=2.3 Hz, 9.0 Hz, 1H, C4-H), 10.10 (s, 1H, NH), 14.14 ppm (s, 1H, Ru=CH).

$^{19}$F-NMR (C$_6$D$_6$): δ=−76.4 ppm (s).

$^{13}$C-NMR (C$_6$D$_6$): δ=19.7 (CH$_3$ Mes), 20.5 ($\underline{C}$H$_3$CHCH$_3$), 23.1 (CH$_3$CH$\underline{C}$H$_3$), 51.2 (CH$_2$ NHC), 81.3 (CH$_3\underline{C}$HCH$_3$), 115.3 (C3, C6), 118.6 (C4), 120.5 (C3'), 121.9 (C4'), 128.8 (CH Mes), 129.5 (C5'), 130.9 (C2'), 131.3 (C5), 137.9 (C Mes), 141.7 (c1), 142.1 (C1'), 151.4 (C2), 154.1 (C6'), 248.1 ppm (Ru=CH).

Ruthenium complex E7

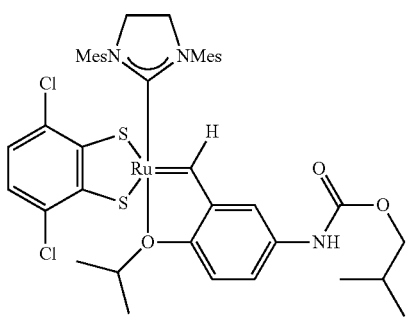

E7 was synthetized according to the general procedure from the particular Ru derivative and isolated in the form of a green solid (100 mg, 0.11 mmol, 76% yield).

$^1$H-NMR (C$_6$D$_6$): δ=0.87 (d, 6H, —C$\underline{H}_3$CHCH$_3$), 1.26 (d, 3H, O—C$\underline{H}_3$CHCH$_3$), 1.37 (d, 3H, O—CH$_3$CHC$\underline{H}_3$), 1.48 (s br, 3H, CH$_3$ Mes), 1.90 (sept, 1H, CH$_3$C$\underline{H}$CH$_3$), 2.06 (s, 6H, CH$_3$ Mes), 2.27 (s br, 3H, CH$_3$ Mes), 2.45 (s br, 3H, CH$_3$ Mes), 2.59 (s br, 3H, CH$_3$ Mes), 3.03 (br, 2H, CH$_2$ NHC), 3.18 (br, 2H, CH$_2$ NHC), 3.99 (m, 2H, O—CH$_2$), 5.34 (sept, 1H, O—CH$_3$C$\underline{H}$CH$_3$), 5.82 (d, J=2.2 Hz, 1H, C6-H), 6.13 (br, 1H, CH Mes), 6.29 (s, 1H, NH), 6.46 (br, 1H, CH Mes), 6.54 (d, J=9.0 Hz, 1H, C3-H), 6.60 (br, 1H, CH Mes), 6.77 (br, 1H, CH Mes), 6.90&7.01 (Abq, 2H, C3'-H, C4'-H), 7.74 (d br, J=9.0 Hz, 1H, C4-H), 14.47 ppm (s, 1H, Ru=CH).

$^{13}$C-NMR (C$_6$D$_6$): δ=20.7 (CH$_3$ Mes), 18.9 ($\underline{C}$H$_3$CH CH$_3$), 20.7 (O—$\underline{C}$H$_3$CHCH$_3$), 23.7 (O—CH$_3$CH$\underline{C}$H$_3$), 28.1 (CH$_3\underline{C}$HCH$_3$), 50.9 (CH$_2$ NHC), 71.0 (O—CH$_2$), 81.3 (O—CH$_3\underline{C}$HCH$_3$), 113.7 (C6), 115.4 (C3), 116.5 (C4), 121.9 (C3'), 123.5 (C4'), 129.1 (CH Mes), 129.2 (CH Mes), 129.4 (CH Mes), 129.6 (CH Mes), 130.0 (C5'), 131.9 (C2'), 133.3 (C5), 141.8 (C1), 142.2 (C1'), 149.6 (C2), 153.2 (NHCOO), 154.6 (C6'), 250.1 ppm (Ru=CH).

Ruthenium complex E8

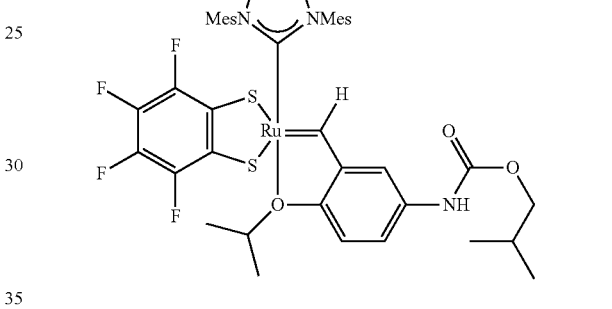

E8 was synthetized according to the general procedure from the particular Ru derivative and isolated in the form of a green solid (137 mg, 0.15 mmol, 78% yield).

$^1$H-NMR (C$_6$D$_6$): δ=0.88 (d, 6H, C$\underline{H}_3$CHCH$_3$), 1.22 (d, 3H, O—C$\underline{H}_3$CHCH$_3$), 1.35 (d, 3H, O—CH$_3$CHC$\underline{H}_3$), 1.45 (br, 3H, CH$_3$ Mes), 1.91 (sept, 1H, CH$_3$C$\underline{H}$CH$_3$), 2.01 (br, 3H, CH$_3$ Mes), 2.06 (br, 3H, CH$_3$ Mes), 2.25 (br, 3H, CH$_3$ Mes), 2.40 (s, 3H, CH$_3$ Mes), 2.47 (s, 3H, CH$_3$ Mes), 3.05 (br m, 4H, CH$_2$ NHC), 3.98 (m, 2H, O—CH$_2$), 5.41 (sept, 1H, O—CH$_3$C$\underline{H}$CH$_3$), 5.78 (d, J=2.3 Hz, 1H, C6-H), 6.06 (br, 1H, CH Mes), 6.37 (s, 1H, NH), 6.47 (br, 1H, CH Mes), 6.53 (d, J=9.0 Hz, 1H, C3-H), 6.56 (br, 1H, CH Mes), 6.75 (br, 1H, CH Mes), 7.74 (br d, J=9.0 Hz, 1H, C4-H), 14.63 ppm (s, 1H, Ru=CH).

$^{13}$C-NMR (C$_6$D$_6$): δ=17.1 (CH$_3$ Mes), 18.4 (CH$_3$ Mes), 19.0 ($\underline{C}$H$_3$CHCH$_3$), 19.3 (CH$_3$ Mes), 20.0 (CH$_3$ Mes), 20.7 (CH$_3$ Mes), 20.7 (CH$_3$ Mes), 20.9 (O—$\underline{C}$H$_3$CHCH$_3$), 23.8 (O—CH$_3$CH$\underline{C}$H$_3$), 51.2 (CH$_2$ NHC), 71.2 (O—CH$_2$), 82.3 (O—CH$_3\underline{C}$HCH$_3$), 113.7 (C6), 115.8 (C3), 117.0 (C4), 129.0 (CH Mes), 129.3 (CH Mes), 129.6 (CH Mes), 129.9 (CH Mes), 133.9 (C5), 134.5 (C Mes), 134.7 (C Mes), 135.1 (C Mes), 135.7 (C Mes), 137.0 (C Mes), 138.2 (C Mes), 138.5 (C Mes), 139.1 (C Mes), 142.0 (C1), 149.8 (C2), 153.9 (NHCOO), 252.3 ppm (Ru=CH).

In a further example, the reaction according to the general procedure is schematically shown in the following scheme using a Ru dichloro complex bearing an NHC ligand containing one nitrogen atom (CAAC ligand) which is reacted with a suitable dithiolate complex:

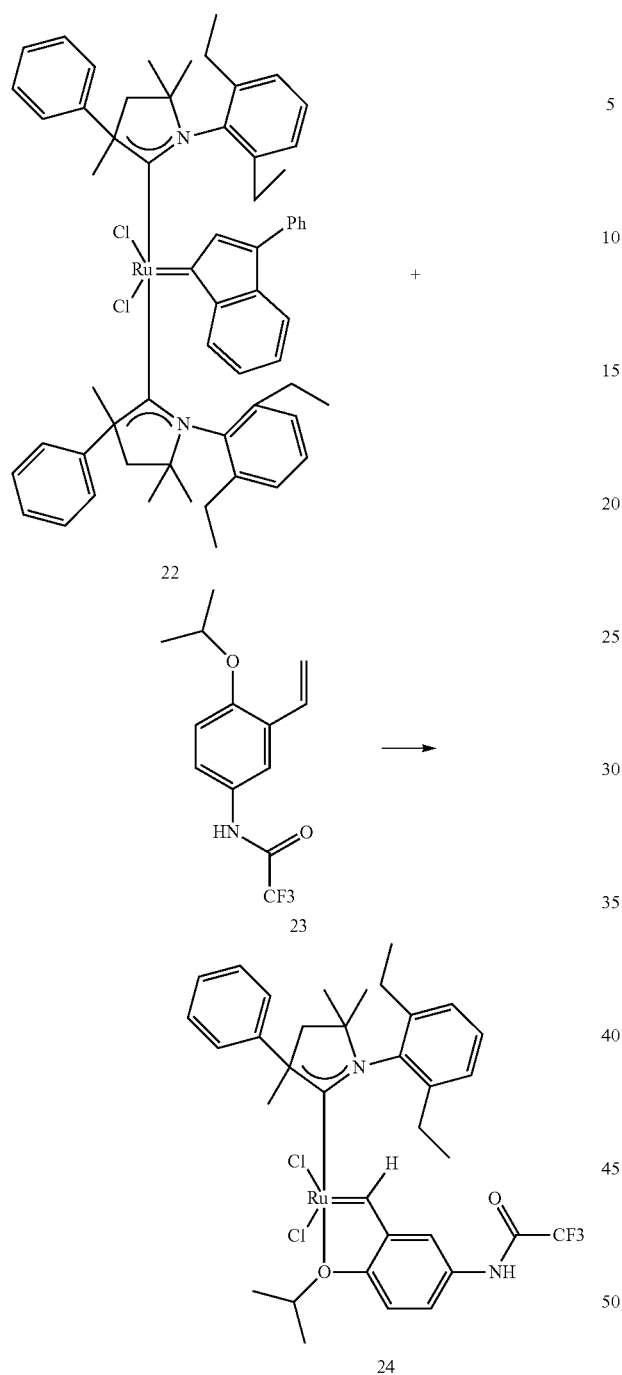

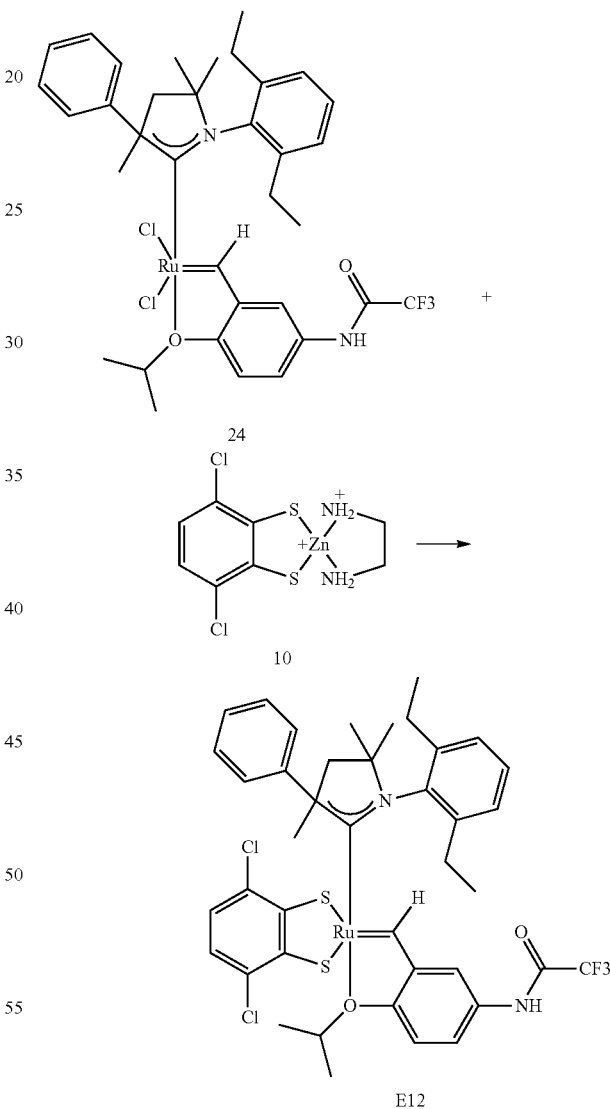

E12

Ruthenium complex 24 was synthetized according to the following steps: Compound 22 (106 mg, 0.106 mmol, 1.0 eq) was added under nitrogen to a solution of 23 (35 mg, 0.127 mmol, 1.2 eq) and suspension of CuCl (21 mg, 0.212 mmol, 2 eq) in benzene (5 mL). The reaction mixture was stirred at 60° C. for 60 minutes. After cooling down to room temperature, the mixture was poured onto silica gel and the product was eluted with Et$_2$O/pentane (3:7 v/v) mixture. Green band was collected and solvents were removed. After drying in high vacuum the green solid 24 was obtained, 30 mg (38%).

$^1$H-NMR (C$_6$D$_6$): δ=0.63 (s, 6H, CH$_3$ CAAC), 0.71 (s, 3H, CH$_3$ CAAC), 1.37 (br, 6H, O—CH$_3$CHCH$_3$), 1.48 (s br, 3H, CH$_3$ CAAC), 1.59&2.02 (ABq, 2H, CH$_2$ CAAC), 2.17 (m, 2H, CH$_2$ Et), 2.38 (m, 2H, CH$_2$ Et), 4.50 (sept, 1H, O—CH$_3$CHCH$_3$), 6.26 (d br, 1H, C3-H), 7.23 (d br, 1H, C4-H), 7.49 (m, 2H, C$_{ortho}$—H Ph), 16.49 ppm (br, 1H, Ru=CH).

$^{13}$C-NMR (C$_6$D$_6$): δ=15.7 (CH$_3$ Et), 21.5 (O—CH$_3$CH CH$_3$), 25.0 (CH$_2$ Et), 26.8 (CH$_3$ CAAC), 27.0 (CH$_3$ CAAC), 29.4 (CH$_3$ CAAC), 50.5 (CH$_2$ CAAC), 60.4 (CCH$_3$Ph), 74.8 (O—CH$_3$CHCH$_3$), 79.8 (NC(CH$_3$)$_2$), 112.7 (C3), 122.2 (C4), 129.5 (C5), 135.9 (C-Et), 139.6 (N—C$_{ipso}$), 140.7 (C2), 143.5 (C1), 145.2 (C$_{ipso}$ Ph), 247.7 ppm (NC: CAAC).

Ruthenium complex E12 was synthetized according to the general procedure and identified without isolation by the characteristic new alkylidene signal at δ=13.85 ppm ($^1$H-NMR (CD$_2$Cl$_2$)s, Ru=CH,):

Exemplary Metathesis Reaction

Z-selective cross-metathesis reaction (CM) between allylbenzene 17 and cis-1,4-butendiol-diacetate 18 to yield (Z)-4-phenyl-2-buteneyl-1-acetate 19 (Z-isomer was confirmed by GC standards):

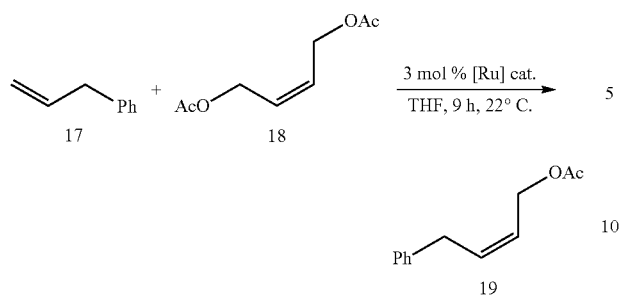

A 3 mol % [Ru] catalyst (complexes E5, E6, E7, E8 according to the invention, and complexes 20 or 21 for comparison) (0.0006 mmol, 3.0 mol %) in THF (290 μL) was transferred by syringe to a vial containing 17 (2.4 mg, 0.02 mmol, 1.00 equiv) and 18 (6.9 mg, 0.04 mmol, 2.00 equiv). The resulting mixture was allowed to stir for 9 hours at 22° C. Analysis of the GC-MS chromatogram revealed surprisingly different yields of the substrate 19 with the different [Ru] catalysts, however the corresponding CM product was obtained in each case in >98:2 Z/E ratio.

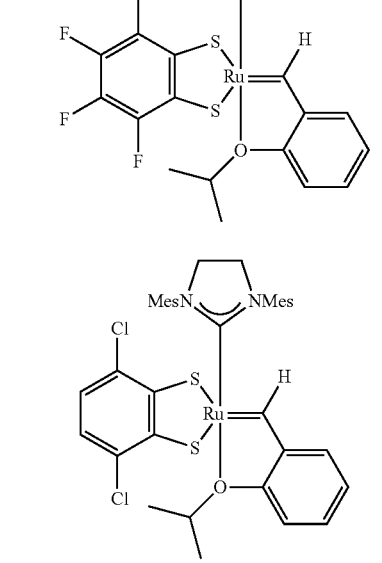

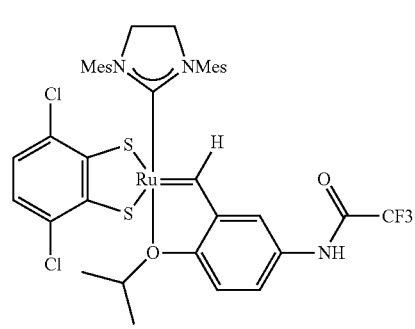

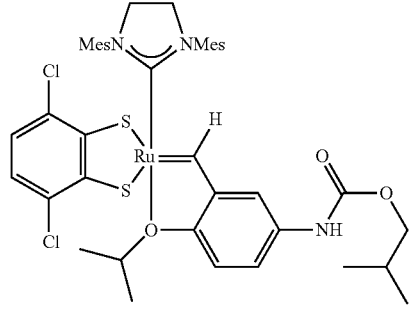

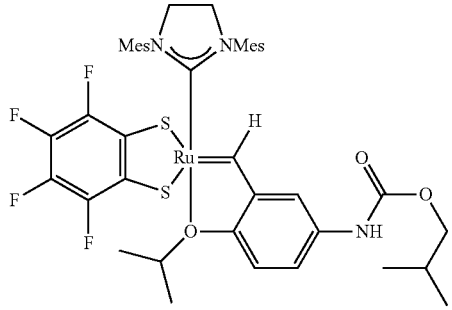

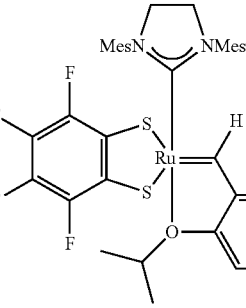
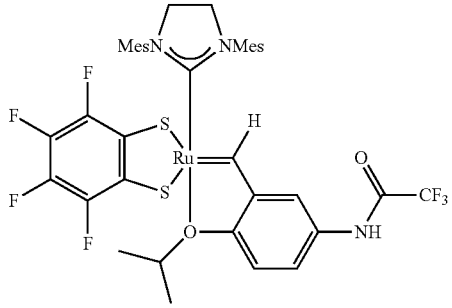

| Catalyst | Yield of 19 [%] | Z/E ratio |
| --- | --- | --- |
| 20 | 46 | >98:2 |
| 21 | 49 | >98:2 |
| E5 | 54 | >98:2 |
| E7 | 54 | >98:2 |
| E8 | 56 | >98:2 |
| E6 | 58 | >98:2 |

Z-selective cross-metathesis reaction (CM) between oct-1-ene 22 and cis-1,4-butendiol-diacetate 18 to yield (Z)-non-2-en-1-yl acetate 23 (Z-isomer was confirmed by GC standards):

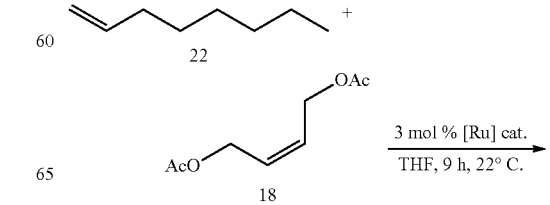

-continued

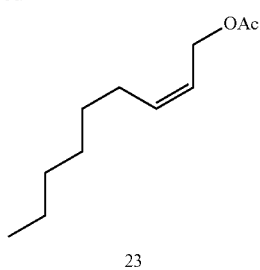

23

A 3 mol % [Ru] catalyst (complexes E5, E7 according to the invention, and complex 21 for comparison) (0.00126 mmol, 3.0 mol %) in THF (290 µL) was transferred by syringe to a vial containing 18 (14.5 mg, 0.084 mmol, 2.00 equiv) and 22 (4.71 mg, 0.042 mmol, 1.00 equiv). The resulting mixture was allowed to stir for 9 hours at 22° C. Analysis of the GC-MS chromatogram revealed surprisingly different yields of the substrate 23 with the different [Ru] catalysts, however the corresponding CM product was obtained in each case in >98:2 Z/E ratio.

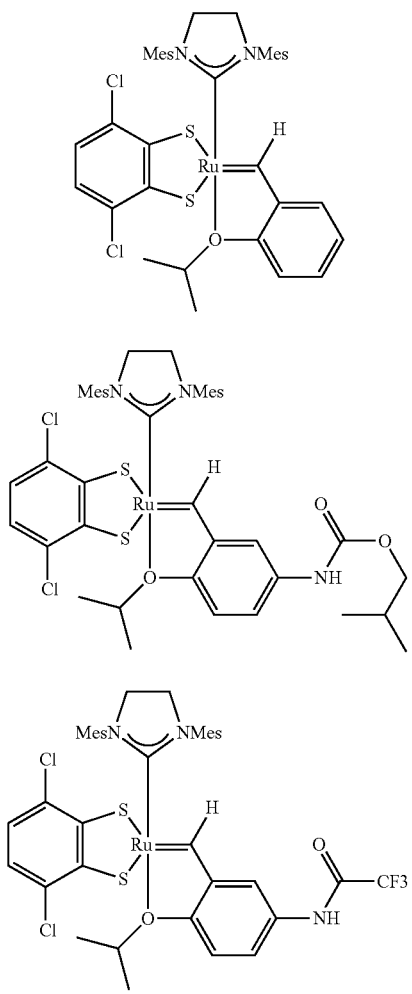

| Catalyst | Yield of 23 [%] | Z/E ratio |
|---|---|---|
| 21 | 64 | >98:2 |
| E7 | 72 | >98:2 |
| E5 | 74 | >98:2 |

As can be seen from compounds E5, E6, E7 and E8 compared to compound 20 and 21, the omission of the amido group results in a drop of yield of target product. Accordingly, one can draw the conclusion from these results that the introduction of an amide function on the styrenyl ether ligand promotes the activation of the catalyst. Besides the significant activation of the catalyst relatively high conversions in very short amounts of time are observed. Under these conditions, an economic impact can be envisaged by significantly reducing the catalytic load in the metathesis reactions compared to the known catalysts lacking the amido group without affecting the yield.

The invention claimed is:

1. A compound of formula 4 or formula 5

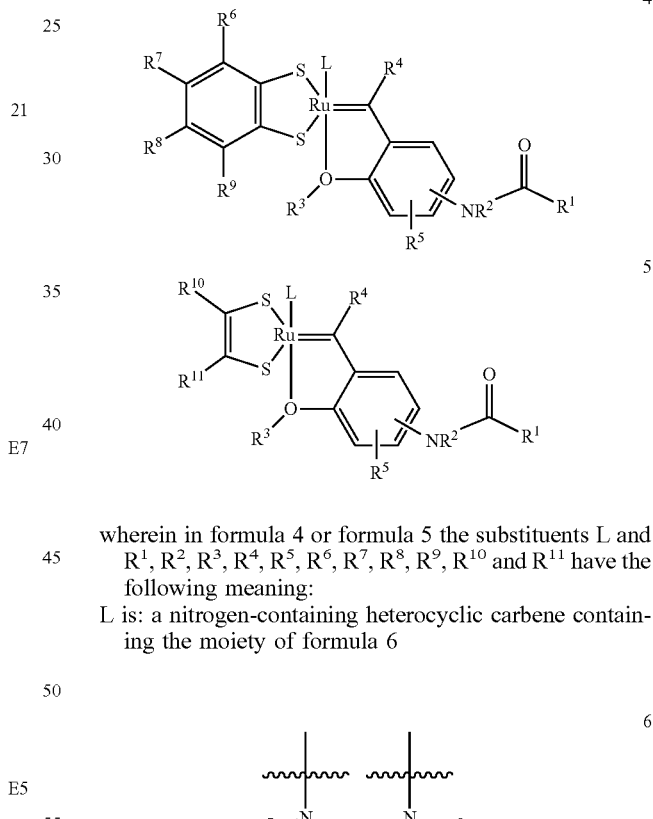

wherein in formula 4 or formula 5 the substituents L and $R^1$, $R^2$, $R^3$, $R^4$, $R^5$, $R^6$, $R^7$, $R^8$, $R^9$, $R^{10}$ and $R^{11}$ have the following meaning:

L is: a nitrogen-containing heterocyclic carbene containing the moiety of formula 6

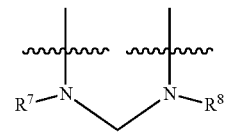

wherein $R^7$ and $R^8$ as defined in formula 6 are each independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen, and wherein the chemical bonds which are symbolized with a wiggly line are connected to an optionally substituted alkenylene or alkylene group, respectively, wherein the carbene carbon atom, the two nitrogen atoms and the optionally substituted alkenylene or alkylene group form a ring; or a nitrogen-containing heterocyclic carbene containing the moiety of formula 7

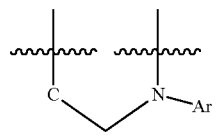

7 wherein Ar as defined in formula 7 is aryl optionally substituted with one or more groups selected from: $C_1$-$C_{12}$ alkyl, $C_1$-$C_{12}$ perfluoroalkyl, alkoxy, $C_6$-$C_{14}$ aryl, $C_6$-$C_{14}$ aryloxy, or halogen; and wherein the chemical bonds which are symbolized with a wiggly line are connected to an optionally substituted alkenylene or alkylene group, respectively, wherein the carbon atom, the carbene carbon atom, the nitrogen atom and the optionally substituted alkenylene or alkylene group form a ring, which may optionally be bridged by an alkylene group;

$R^1$ is: $C_{1-6}$ alkyl or alkoxy, each of which is optionally substituted with one or more of halogen; or phenyl, optionally substituted with one or more of unbranched or branched $C_{1-20}$ alkyl or unbranched or branched $C_{1-20}$ alkoxy, $C_{5-9}$ cycloalkyl or $C_{5-9}$ cycloalkoxy, aryl, aryloxy, unbranched or branched $C_{1-20}$ alkylcarbonyl, arylcarbonyl, unbranched or branched $C_{1-20}$ alkoxycarbonyl, aryloxycarbonyl, heteroaryl, carboxyl, cyano, nitro, amido, aminosulfonyl, N-heteroarylsulfonyl, unbranched or branched $C_{1-20}$ alkylsulfonyl, arylsulfonyl, unbranched or branched $C_{1-20}$ alkylsulfinyl, arylsulfinyl, unbranched or branched $C_{1-20}$ alkylthio, arylthio, sulfonamide, halogen or $N(R^y)(R^z)$, wherein $R^y$ and $R^z$ are independently selected from H and $C_{1-20}$ alkyl;

$R^2$ is: H and $NR^2$—C(O)—$R^1$ is in para-position with respect to O;

$R^3$ is: methyl or isopropyl;

$R^4$ and $R^5$ are: H;

$R^6$, $R^7$, $R^8$, and $R^9$ in formula 4 are independently selected from H and halogen;

$R^{10}$ and $R^{11}$ in formula 5 are independently selected from halogen and cyano.

2. The compound of claim 1, wherein the carbene of formula 6 is a carbene of one of formulas 6a, 6b, 6c or 6d:

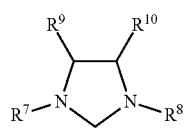

6a

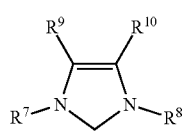

6b

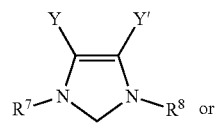

6c

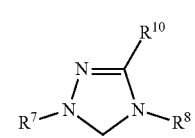

6d wherein $R^9$ and $R^{10}$ are each independently H, unbranched or branched $C_{1-20}$ alkyl, or phenyl, wherein phenyl is optionally substituted with up to three groups independently selected from unbranched or branched $C_{1-6}$ alkyl, $C_{1-6}$ alkoxy or halogen; or $R^9$ and $R^{10}$ together with the carbon atoms to which they are attached are combined to form a carbocyclic 3 to 8 membered ring;

Y and Y' are halogen.

3. The compound of claim 2, wherein L is of formula 6a or 6b, and $R^9$ and $R^{10}$ as defined in formula 6a or 6b are H, respectively, and $R^7$ and $R^8$ as defined in formula 6a and 6b are mesityl, or 2,6-diisopropylphenyl; or wherein L is of formula

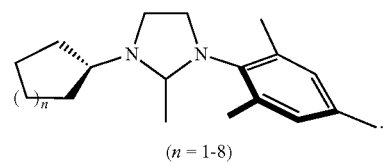

(n = 1-8)

4. The compound of claim 1, wherein the carbene of formula 7 is a carbene of one of formulas 7a or 7b:

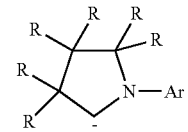

7a wherein each R in formula 7a is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein two R which are separated by the C—$CR_2$—C moiety can be combined to form a cyclic system; or a carbene of formula 7b

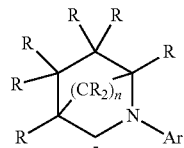

wherein each R in formula 7b is independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein n is 1, 2 or 3.

5. The compound of claim 4, wherein the carbene of formula 7a is of formula 7a'

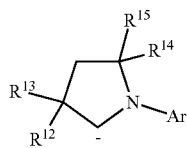

wherein $R^{12}$, $R^{13}$, $R^{14}$, and $R^{15}$ in formula 7a' are each independently hydrogen, $C_1$-$C_{12}$ alkyl, $C_3$-$C_{12}$ cycloalkyl, $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom; and wherein $R^{12}$ and/or $R^{13}$ can be combined with $R^{14}$ and/or $R^{15}$ to form a cyclic system; or wherein the carbene of formula 7b is of formula 7b':

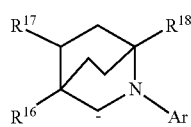

wherein $R^{16}$, $R^{17}$ and $R^{18}$ in formula 7b' are each independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom.

6. The compound of claim 1, wherein L in formula 4 or 5 is a carbene of formula 7c

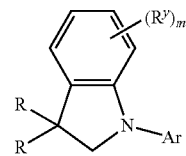

wherein in formula 7c m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen;

or is a carbene of formula 7d

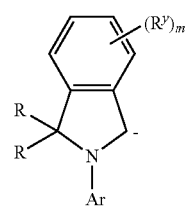

wherein in formula 7d m is an integer of from 0 to 4, and each $R^y$ independently has the meaning of $C_1$-$C_{12}$ alkyl, $C_1$-$C_{12}$ perfluoroalkyl, $C_1$-$C_{12}$ alkoxy, $C_6$-$C_{14}$ aryl, $C_6$-$C_{14}$ aryloxy, or halogen;

or is a carbene of formula 7e

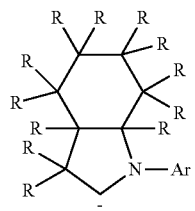

or is a carbene of formula 7f

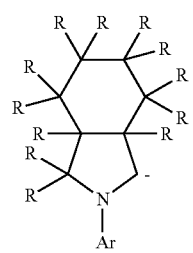

or is a carbene of formula 7g or 7h

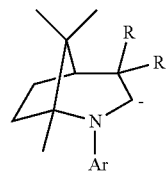

7g

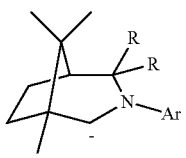

7h or is a carbene of formula 7i

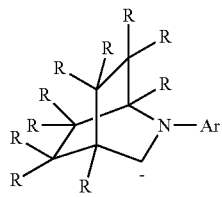

7i or is a carbene of formula 7k

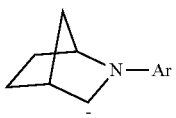

7k and wherein each R in one of formulas 7c to 7i is independently hydrogen or $C_1$-$C_{12}$ alkyl, or $C_3$-$C_{12}$ cycloalkyl, or $C_2$-$C_{12}$ alkenyl, $C_6$-$C_{14}$ aryl, $C_1$-$C_5$ perfluoroalkyl, $C_7$-$C_{24}$ aralkyl, or $C_6$-$C_{14}$ perfluoroaryl group, which are optionally substituted with at least one $C_1$-$C_{12}$ alkyl, $C_1$-$C_{12}$ perfluoroalkyl, $C_1$-$C_{12}$ alkoxy, $C_6$-$C_{14}$ aryloxy, or a halogen atom.

7. The compound of claim 1, wherein the compound is selected from one of compounds E1 to E12:

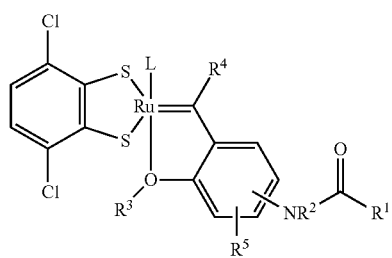

E1

-continued

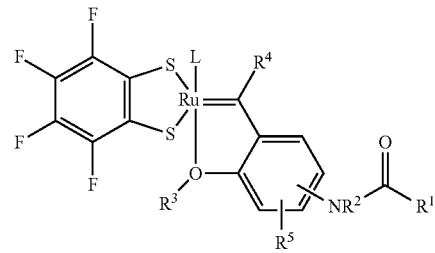

E2

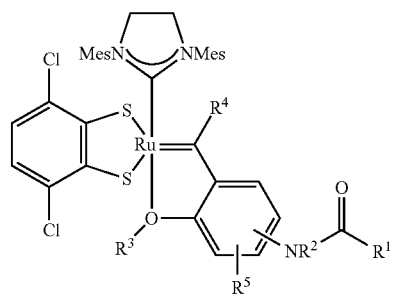

E3

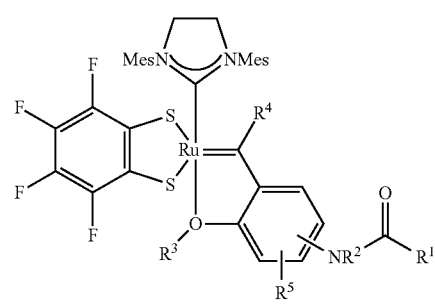

E4

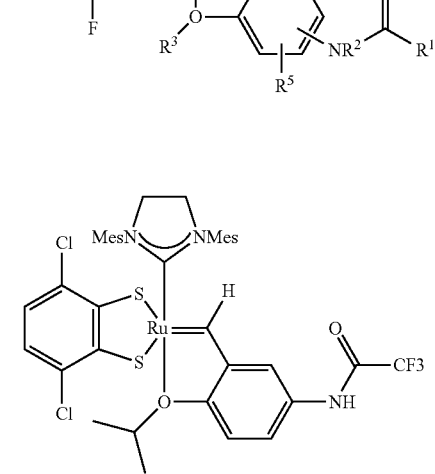

E5

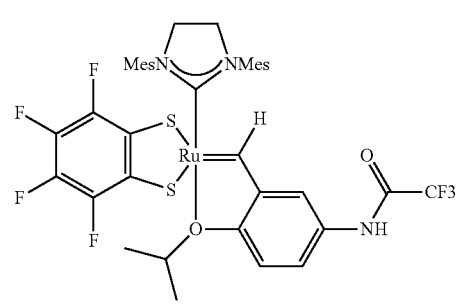

E6

-continued

E7

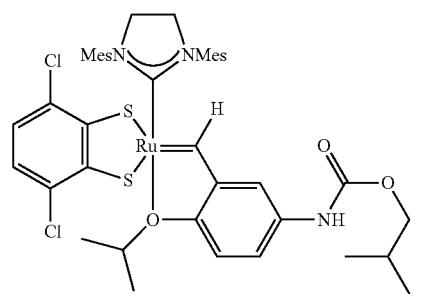

E8

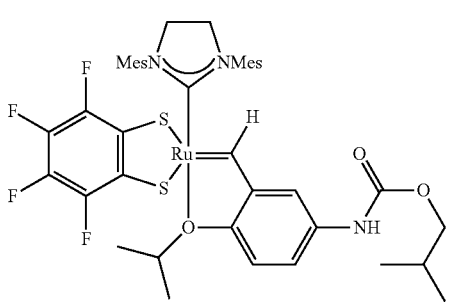

E9

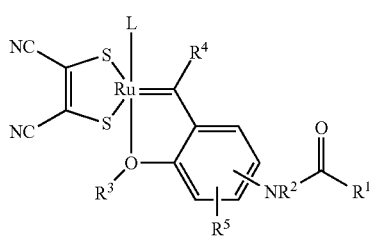

E10

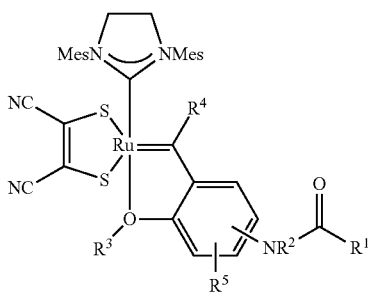

E11

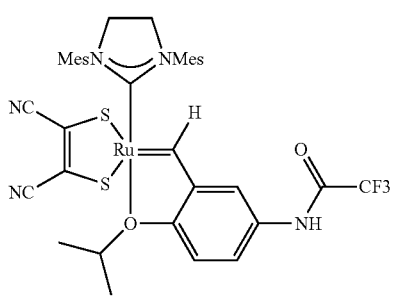

-continued

E12

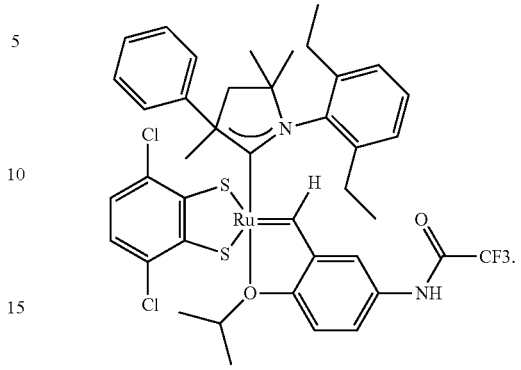

8. The compound of claim 1, wherein the compound is immobilized on a solid support.

9. A method of catalysing a metathesis reaction, comprising reacting one or more olefins in the presence of a compound as defined in claim 1.

10. The method of claim 9, wherein more than 80% of olefins formed in the catalysed metathesis reaction are Z-olefins.

11. The compound of claim 1, wherein the aryl of formula 7 is phenyl.

12. The compound of claim 2, wherein $R^9$ and $R^{10}$ together with the carbon atoms to which they are attached are combined to form an aryl ring.

13. The compound of claim 12, wherein the aryl ring is $C_6H_4$.

14. The compound of claim 4, wherein the carbene of formula 7 is a carbene of formula 7b and wherein R in formula 7b are each independently hydrogen, $C_1$-$C_{12}$ alkyl, or $C_3$-$C_{12}$ cycloalkyl.

15. The compound of claim 5, wherein the carbene of formula 7b is of formula 7b' and wherein $R^{16}$, $R^{17}$ and $R^{18}$ in formula 7b' are each independently hydrogen, $C_1$-$C_{12}$ alkyl, or $C_3$-$C_{12}$ cycloalkyl.

16. The compound of claim 6, wherein each R in formulas 7c to 7i is hydrogen, $C_1$-$C_{12}$ alkyl, or $C_3$-$C_{12}$ cycloalkyl.

17. The compound of claim 6, wherein the carbene of formula 7c is a carbene of formula 7c'

7c'

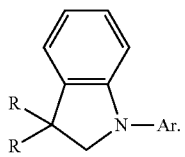

18. The compound of claim 6, wherein the carbene of formula 7d is a carbene of formula 7d'
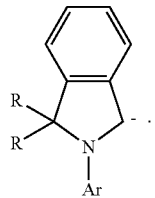
7d'

UNITED STATES PATENT AND TRADEMARK OFFICE
CERTIFICATE OF CORRECTION

PATENT NO. : 10,688,481 B2
APPLICATION NO. : 16/333341
DATED : June 23, 2020
INVENTOR(S) : Eros et al.

It is certified that error appears in the above-identified patent and that said Letters Patent is hereby corrected as shown below:

On the Title Page

Assignee: reads, "XiMo AG" which should read, "Verbio Vereinigte BioEnergie AG"

In the Specification

Column 5, Line 5 appearing as:

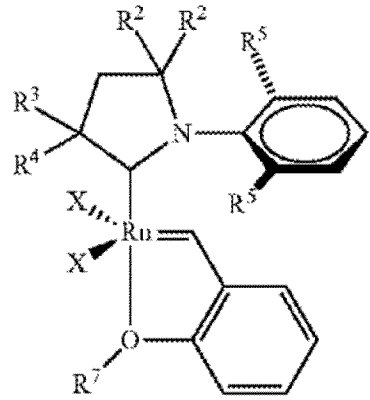

Should be:

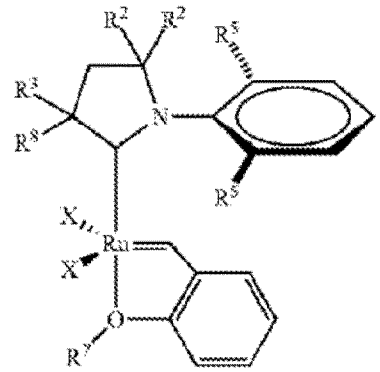

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*

Column 5, Line 30 appearing as:

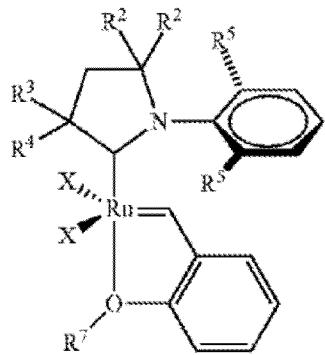

Should be:

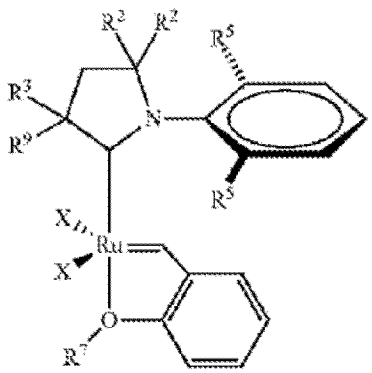

Column 6, Line 63 reads, "... R9, R19..." which should read, "... R9, R10..."

Column 8, Line 44 reads, "R9 and R19 together..." which should read, "R9 and R10 together..."

Column 8, Line 51 reads, "... wherein R9 and R19..." which should read, "... wherein R9 and R10..."

Column 8, Line 53 reads, "R9 as defined..." which should read, "R8 as defined..."

Column 23, Line 47 reads, 2nd occurrence "... and $C_5F_{17}$." which should read, "... and $C_8F_{17}$."

Column 23, Line 53 reads, "...and $C_5F_{17}$." which should read, "...and $C_8F_{17}$."

Column 25, Line 30 reads, "... R7 and R9 ..." which should read, "... R7 and R8 ..."

Column 35, Line 48 reads, "... —OR, —C(O)R, ..." which should read, "... —OR, —OC(O)R ..."

Column 36, Line 41 reads, "... —OR, —OC(O)R, —C(O)OR," which should read, "... —OR, —OC(O)R, —OC(O)OR,"

Column 36, Line 42 reads, "—C(O)N(R')$_2$, —OSiI$_3$, ..." which should read, "—OC(O)N(R')$_2$, —OSiI$_3$, ..."

In the Claims

Column 51, Line 18 Claim 1 reads, "... $C_1$-$C_{12}$ perfluoralkyl, alkoxy ..." which should read, "... $C_1$-$C_{12}$ perfluoralkyl, $C_1$-$C_{12}$ alkoxy ..."